US011202607B2

(12) United States Patent
Hamade et al.

(10) Patent No.: US 11,202,607 B2
(45) Date of Patent: Dec. 21, 2021

(54) BIOLOGICAL INFORMATION ACQUISITION DEVICE AND BIOLOGICAL INFORMATION ACQUISITION METHOD

(71) Applicant: SEIKO EPSON CORPORATION, Tokyo (JP)

(72) Inventors: Yuiga Hamade, Chino (JP); Yasunori Koide, Matsumoto (JP); Takashi Toya, Chino (JP)

(73) Assignee: SEIKO EPSON CORPORATION, Tokyo (JP)

( * ) Notice: Subject to any disclaimer, the term of this patent is extended or adjusted under 35 U.S.C. 154(b) by 448 days.

(21) Appl. No.: 16/305,552

(22) PCT Filed: May 19, 2017

(86) PCT No.: PCT/JP2017/018868
§ 371 (c)(1),
(2) Date: Nov. 29, 2018

(87) PCT Pub. No.: WO2017/208860
PCT Pub. Date: Dec. 7, 2017

(65) Prior Publication Data
US 2019/0254597 A1    Aug. 22, 2019

(30) Foreign Application Priority Data
May 30, 2016    (JP) .............................. JP2016-107007

(51) Int. Cl.
*A61B 5/00*    (2006.01)
*A61B 5/145*    (2006.01)
*A61B 5/1455*    (2006.01)

(52) U.S. Cl.
CPC ............ *A61B 5/681* (2013.01); *A61B 5/1455* (2013.01); *A61B 5/14532* (2013.01);
(Continued)

(58) Field of Classification Search
CPC ... A61B 5/681; A61B 5/1455; A61B 5/14532; A61B 5/14552; A61B 5/489;
(Continued)

(56) References Cited

U.S. PATENT DOCUMENTS

2006/0129037 A1*    6/2006  Kaufman ............. A61B 5/1455
                                                               600/322
2007/0015980 A1*    1/2007  Numada ............ A61B 5/14552
                                                               600/322
(Continued)

FOREIGN PATENT DOCUMENTS

CN    103260515 A    8/2013
JP    H10-216112 A    8/1998
(Continued)

OTHER PUBLICATIONS

Aug. 15, 2017 International Search Report issued in International Patent Application No. PCT/JP2017/018868.

*Primary Examiner* — Eric F Winakur
*Assistant Examiner* — Abid A Mustansir
(74) *Attorney, Agent, or Firm* — Oliff PLC

(57) ABSTRACT

A technique for realizing energy saving. According to a biological information acquisition device, light emitting power per unit area of one light emitting element emitting light when first biological information is acquired is weaker than light emitting power per unit area of one light emitting element emitting light when second biological information is acquired.

17 Claims, 11 Drawing Sheets

(52) U.S. Cl.
CPC ......... *A61B 5/14552* (2013.01); *A61B 5/489* (2013.01); *A61B 2560/0209* (2013.01); *A61B 2560/0214* (2013.01)

(58) Field of Classification Search
CPC .... A61B 2560/0209; A61B 2560/0214; A61B 2560/0475; A61B 2562/063
See application file for complete search history.

(56) References Cited

U.S. PATENT DOCUMENTS

| | | | |
|---|---|---|---|
| 2007/0085995 A1* | 4/2007 | Pesach | G01N 33/66 356/39 |
| 2013/0102907 A1 | 4/2013 | Funane et al. | |
| 2013/0261413 A1 | 10/2013 | Kawahara et al. | |
| 2015/0216454 A1 | 8/2015 | Kasahara et al. | |
| 2016/0098834 A1 | 4/2016 | Eguchi et al. | |
| 2017/0065177 A1* | 3/2017 | Sugi | A61B 5/489 |

FOREIGN PATENT DOCUMENTS

| | | |
|---|---|---|
| JP | 2007-044491 A | 2/2007 |
| JP | 2014-124454 A | 7/2014 |
| JP | 2014-124455 A | 7/2014 |
| JP | 2015-142666 A | 8/2015 |
| JP | 2016-073483 A | 5/2016 |
| WO | 2012/005303 A1 | 1/2012 |

\* cited by examiner

[Fig. 1]
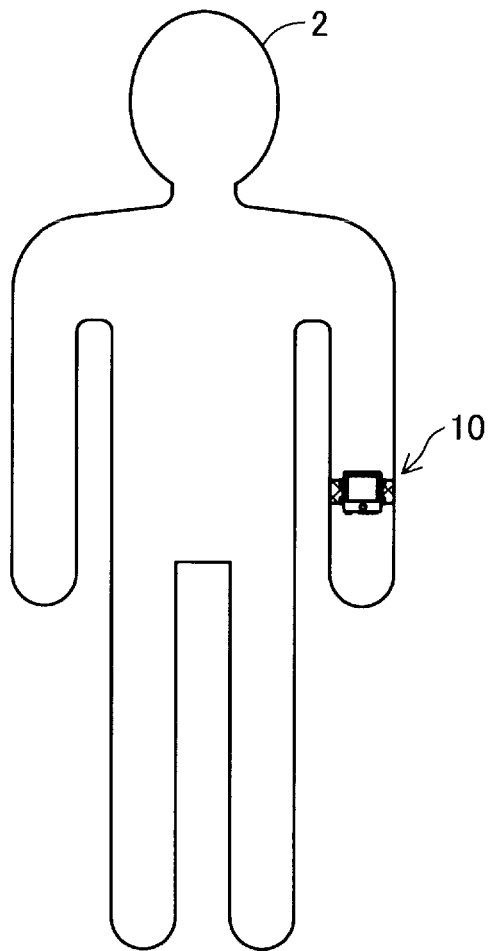
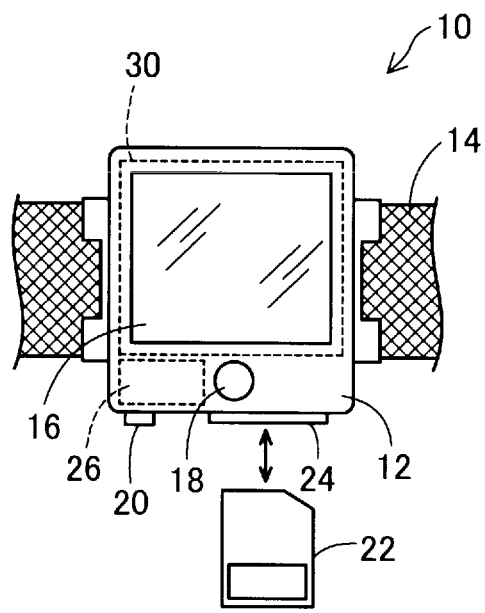
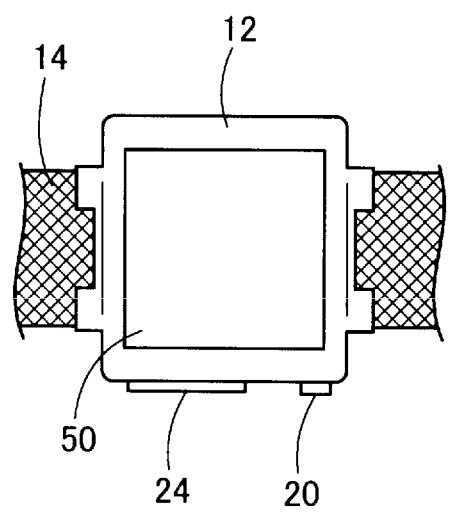

[Fig. 2]
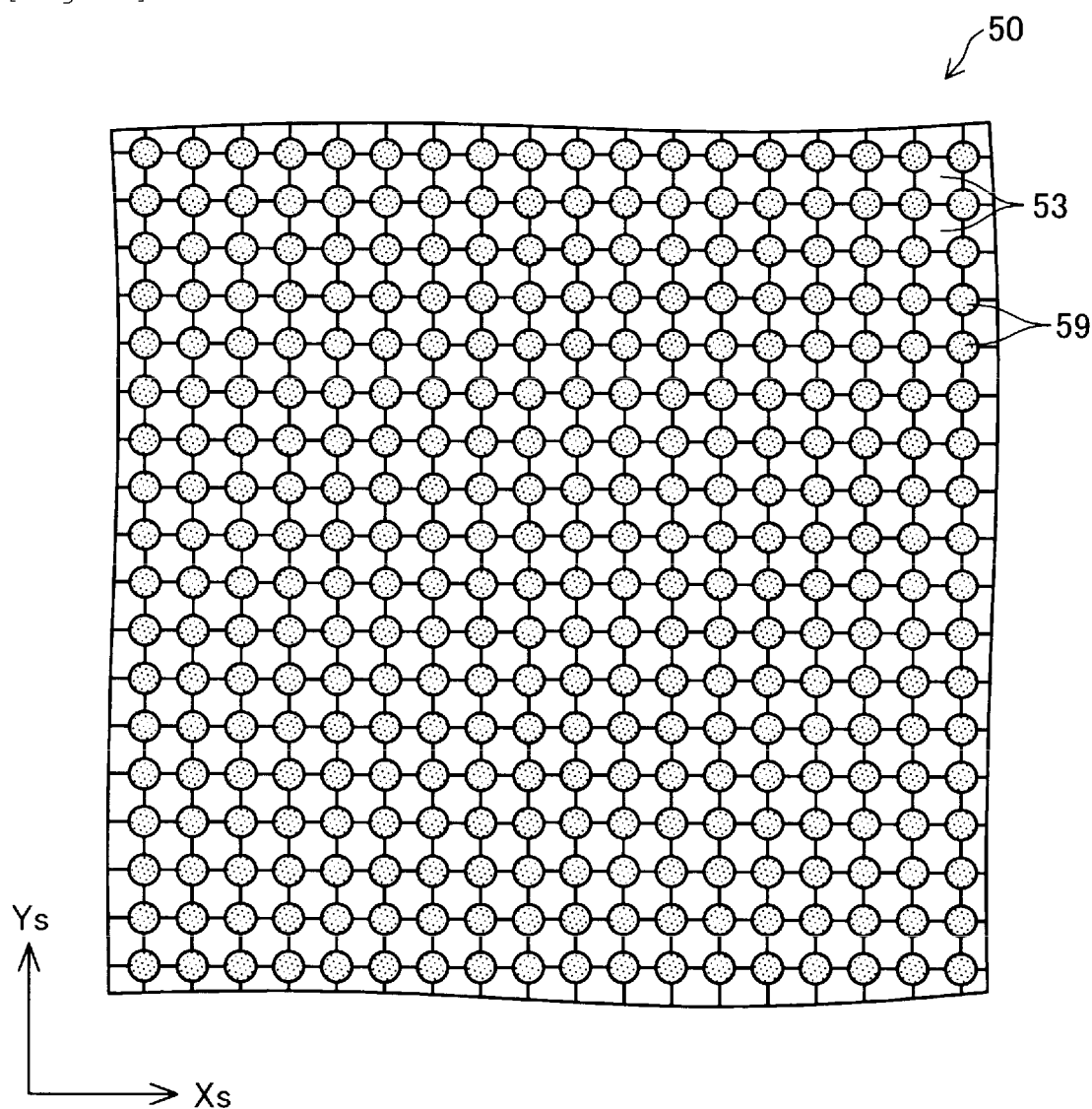

[Fig. 3]
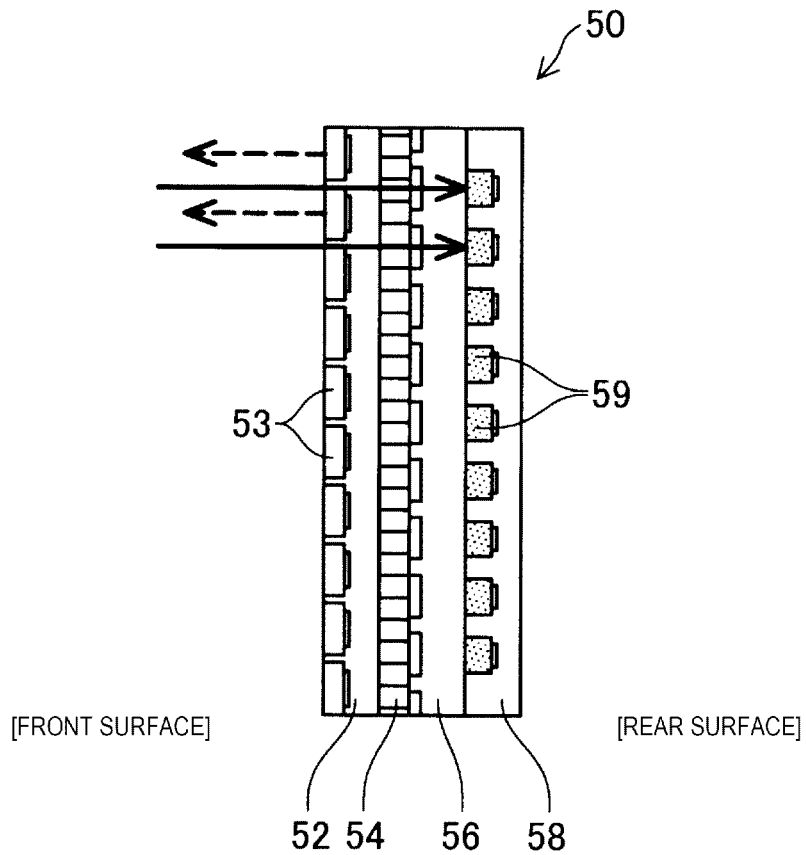
[FRONT SURFACE]　　　　　　　　　　[REAR SURFACE]
52　54　　56　　58
[Fig. 4]
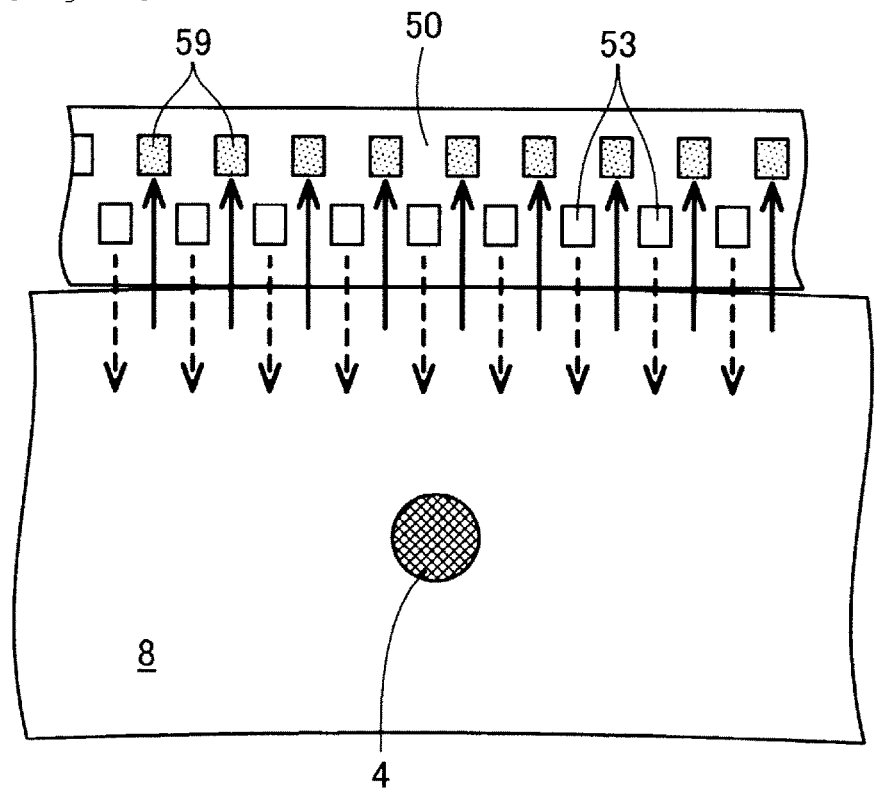

[Fig. 5]
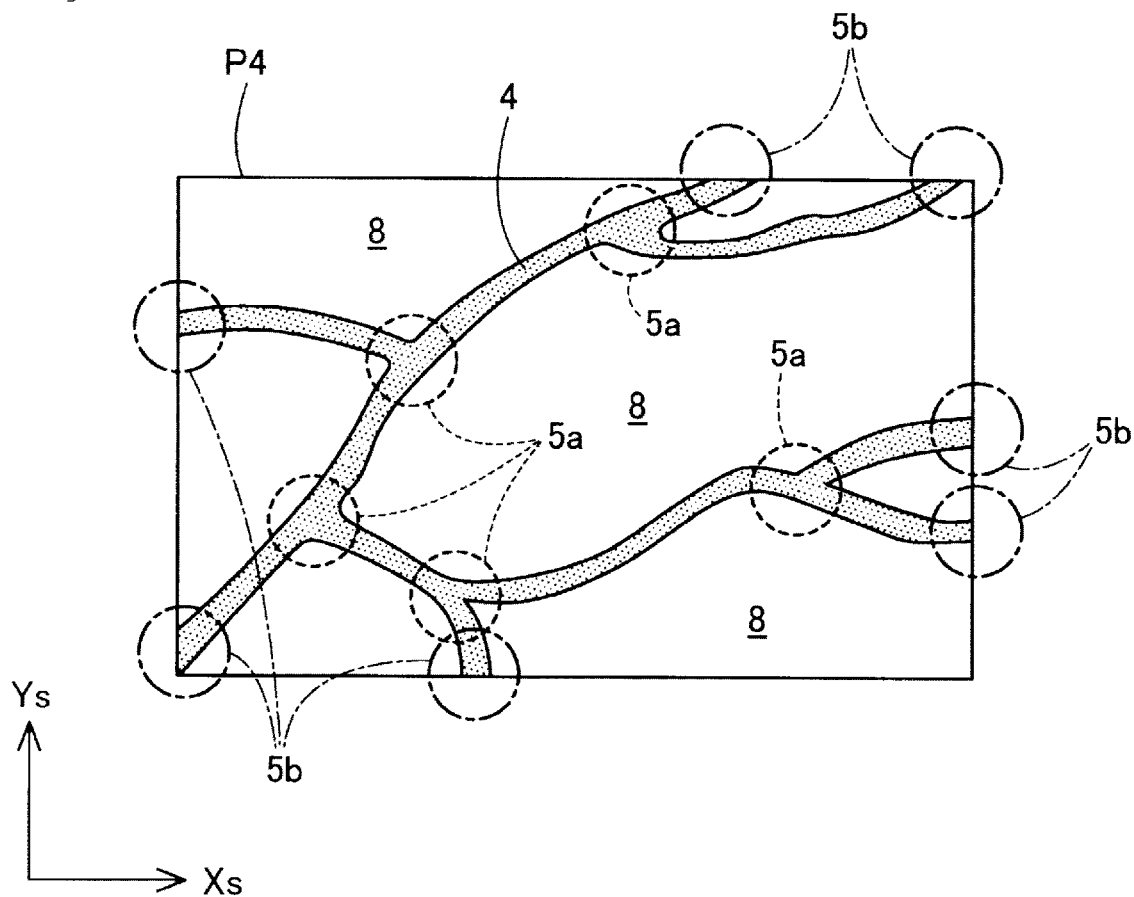
[Fig. 6]
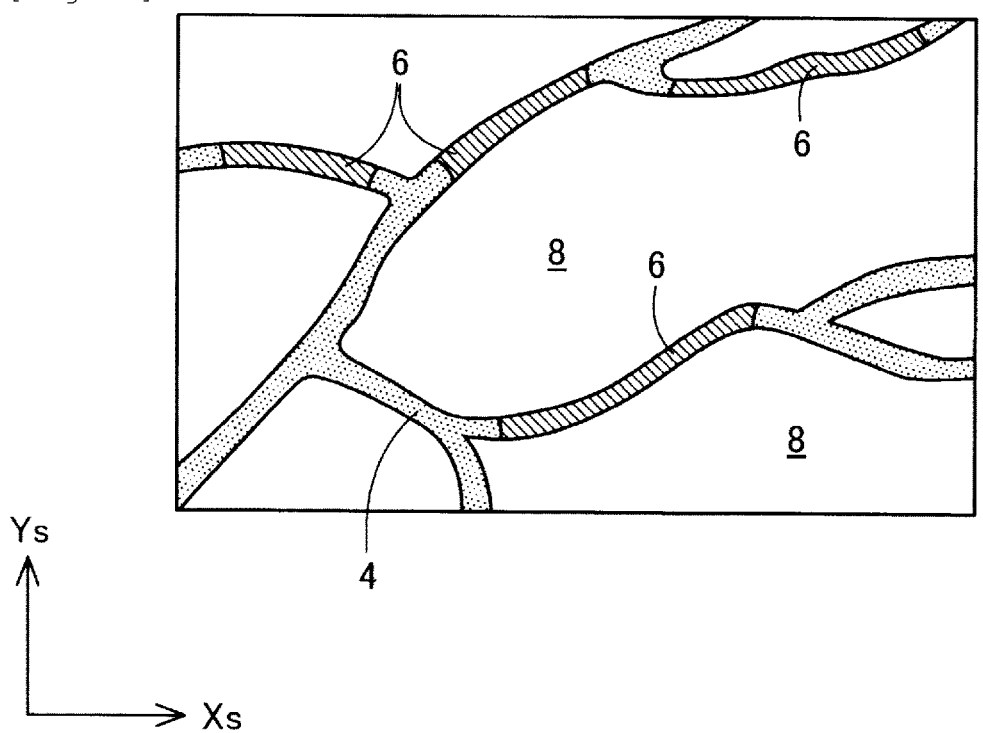

[Fig. 7]
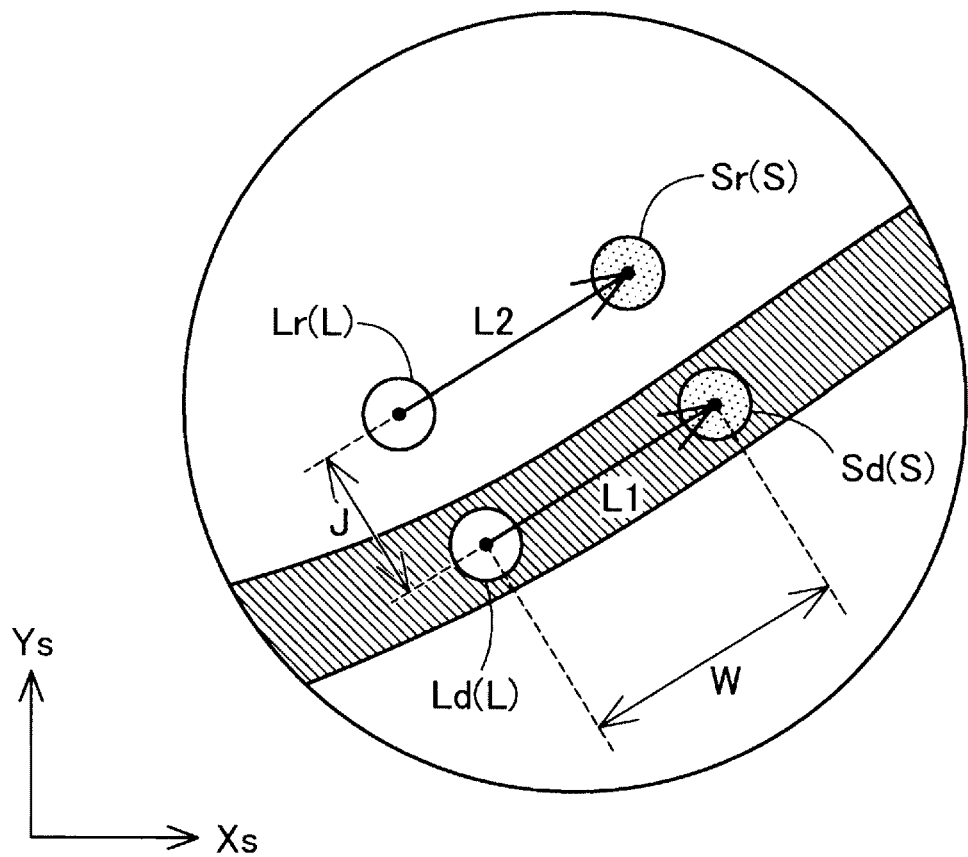
[Fig. 8]
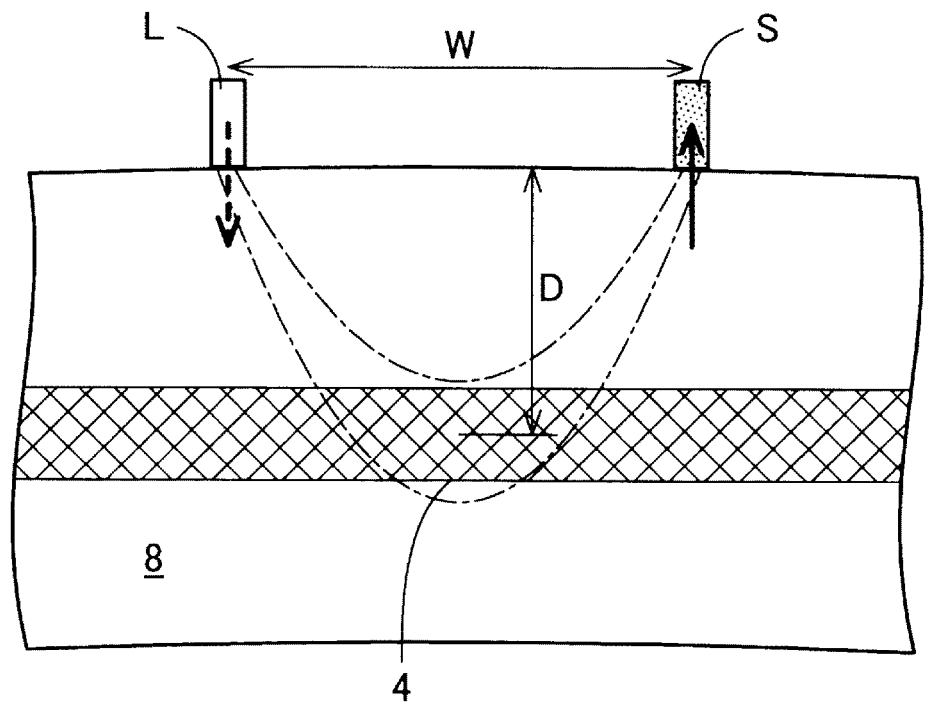

[Fig. 9]
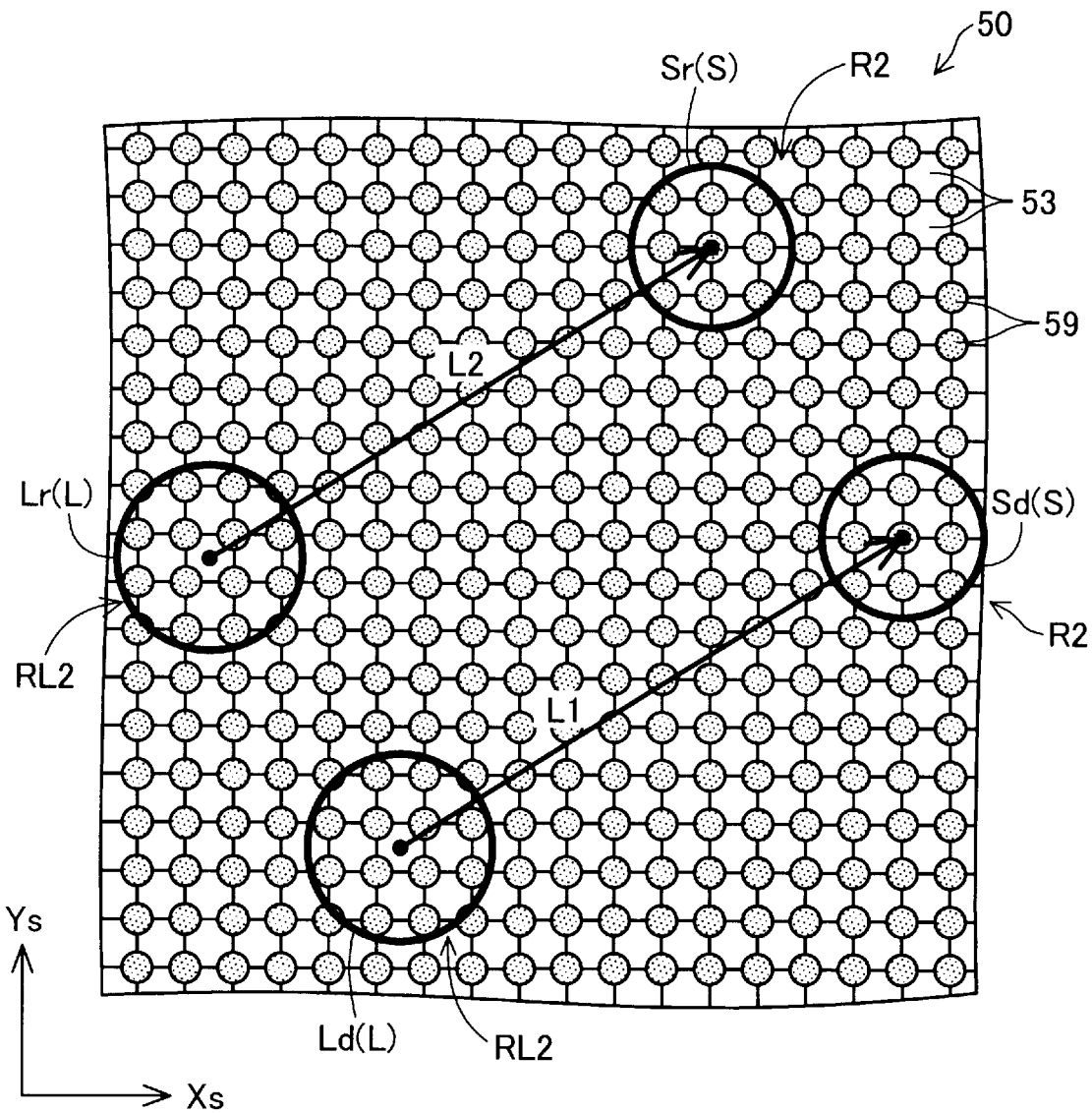

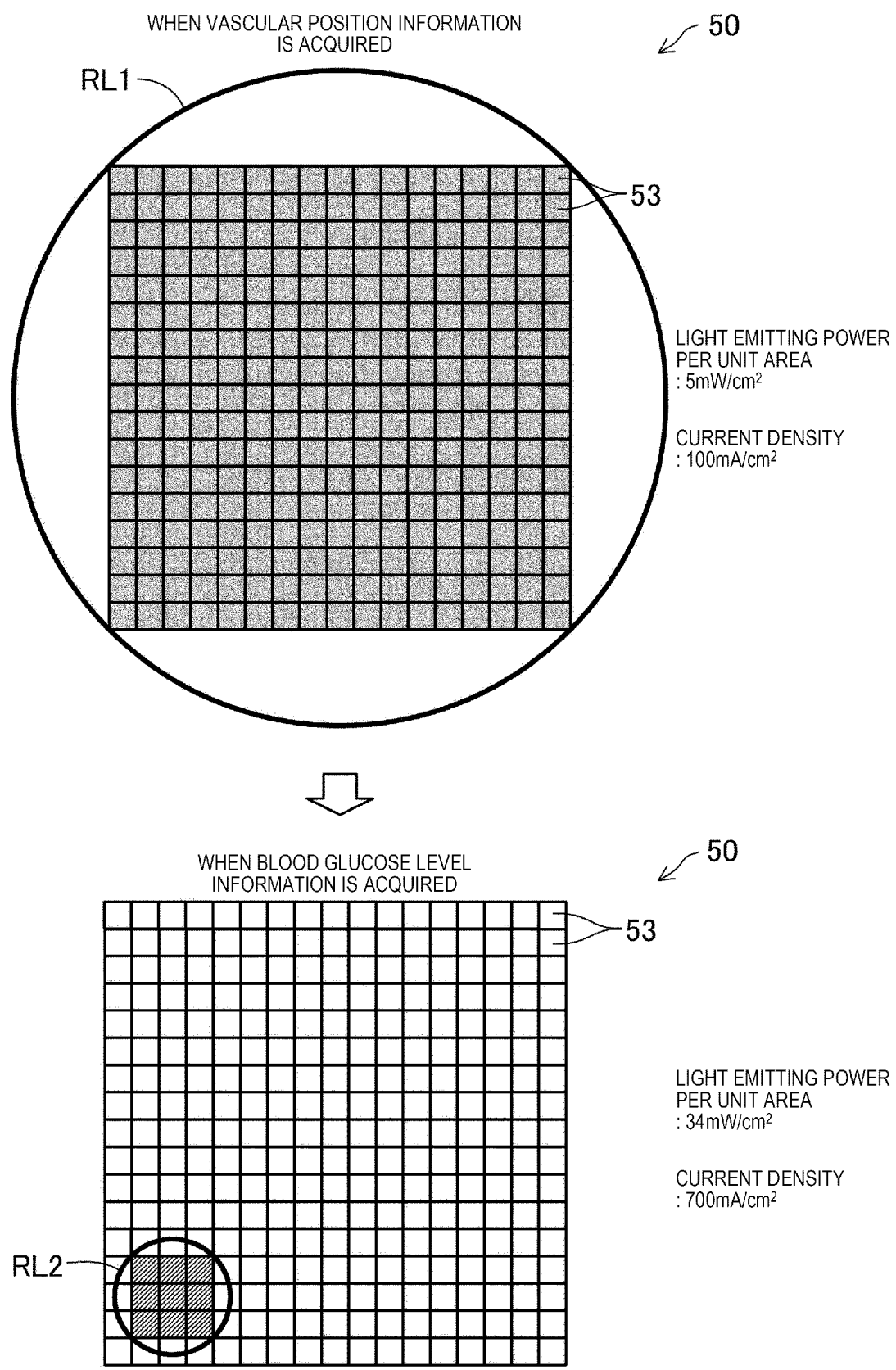
[Fig. 10]

[Fig. 11]

| | | NET LIGHT EMITTING AREA (cm²) | CURRENT DENSITY (mA/cm²) | APPLIED CURRENT (mA) | DRIVE VOLTAGE (V) | POWER CONSUMPTION (mW) | POWER DENSITY (mW/cm²) | LIGHT EMITTING POWER PER UNIT AREA (mW/cm²) | LIGHT EMITTING POWER (mW) | LIGHT EMITTING AREA INSIDE CIRCUMSCRIBED CIRCLE (cm²) | LIGHT EMITTING POWER PER LIGHT EMITTING REGION (mW/cm²) | SURFACE TEMPERATURE (°C) |
|---|---|---|---|---|---|---|---|---|---|---|---|---|
| APPLICATION EXAMPLE 1 | WHEN VASCULAR POSITION INFORMATION IS ACQUIRED | 1.2 | 100 | 120 | 4.3 | 516 | 430 | 5 | 6 | 1.884 | 3.185 | 39 |
| | WHEN BLOOD GLUCOSE LEVEL INFORMATION IS ACQUIRED | 0.012 | 700 | 8.4 | 6.5 | 54.6 | 4550 | 34 | 0.408 | 0.019 | 21.656 | 37 |
| APPLICATION EXAMPLE 2 | WHEN VASCULAR POSITION INFORMATION IS ACQUIRED | 1.2 | 100 | 120 | 4.3 | 516 | 430 | 5 | 6 | 1.884 | 3.185 | 39 |
| | WHEN BLOOD GLUCOSE LEVEL INFORMATION IS ACQUIRED | 0.012 | 420 | 5.04 | 5.9 | 29.736 | 2478 | 20 | 0.24 | 0.019 | 12.632 | 31 |
| APPLICATION EXAMPLE 3 | WHEN VASCULAR POSITION INFORMATION IS ACQUIRED | 1.2 | 100 | 120 | 4.3 | 516 | 430 | 5 | 6 | 1.884 | 3.185 | 39 |
| | WHEN BLOOD GLUCOSE LEVEL INFORMATION IS ACQUIRED | 0.012 | 210 | 2.52 | 5.1 | 12.852 | 1071 | 10 | 0.12 | 0.019 | 6.316 | 28 |
| APPLICATION EXAMPLE 4 | WHEN VASCULAR POSITION INFORMATION IS ACQUIRED | 1.2 | 20 | 24 | 4 | 96 | 80 | 1 | 1.2 | 1.884 | 0.637 | 28 |
| | WHEN BLOOD GLUCOSE LEVEL INFORMATION IS ACQUIRED | 0.012 | 210 | 2.52 | 5.1 | 12.852 | 1071 | 10 | 0.12 | 0.019 | 6.316 | 28 |
| COMPARATIVE EXAMPLE | WHEN VASCULAR POSITION INFORMATION IS ACQUIRED | 1.2 | 700 | 840 | 6.5 | 5460 | 4550 | 34 | 40.8 | 1.884 | 21.656 | >100 |
| | WHEN BLOOD GLUCOSE LEVEL INFORMATION IS ACQUIRED | 0.012 | 700 | 8.4 | 6.5 | 54.6 | 4550 | 34 | 0.408 | 0.019 | 21.474 | 37 |

[Fig. 12]
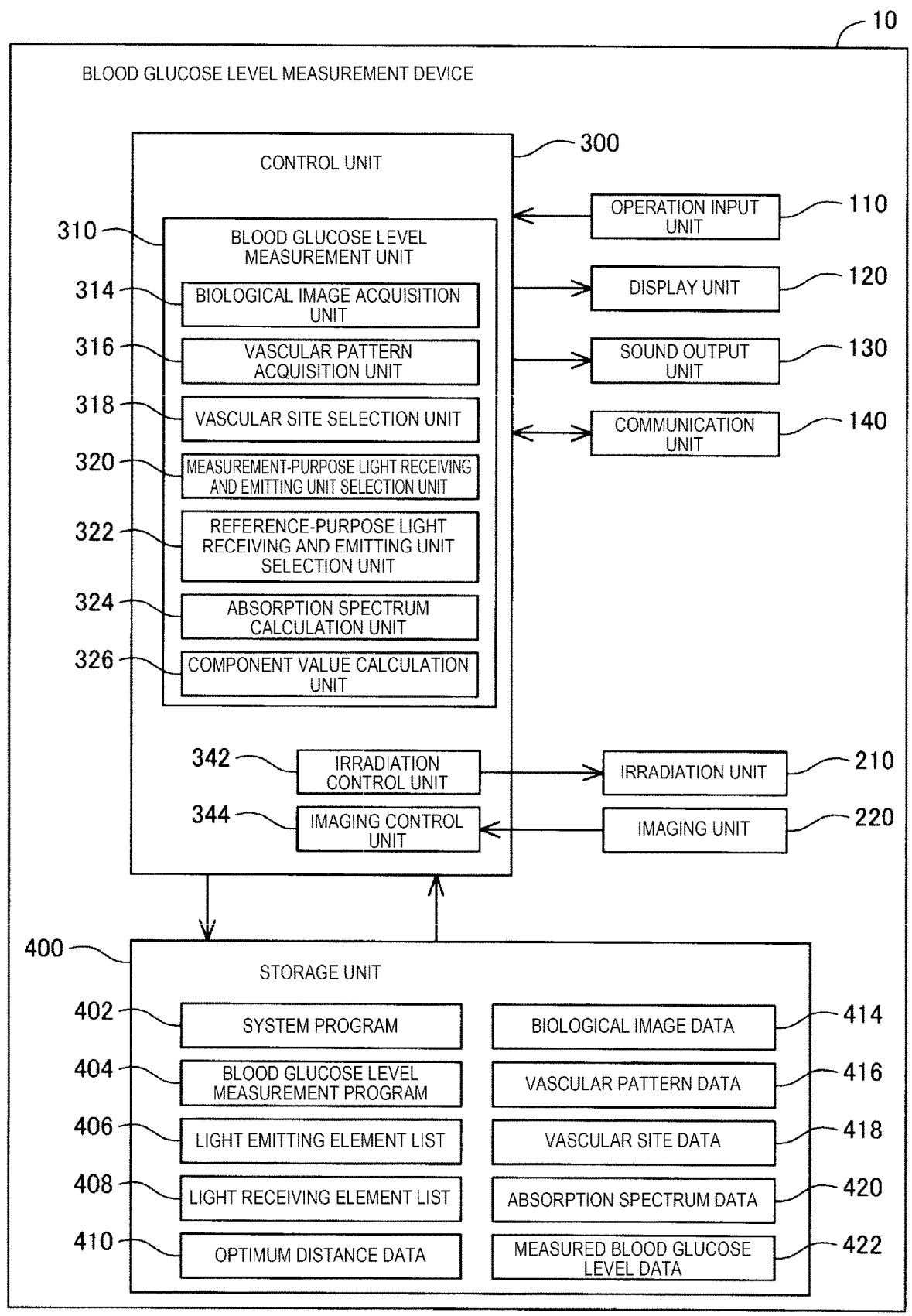

[Fig. 13]
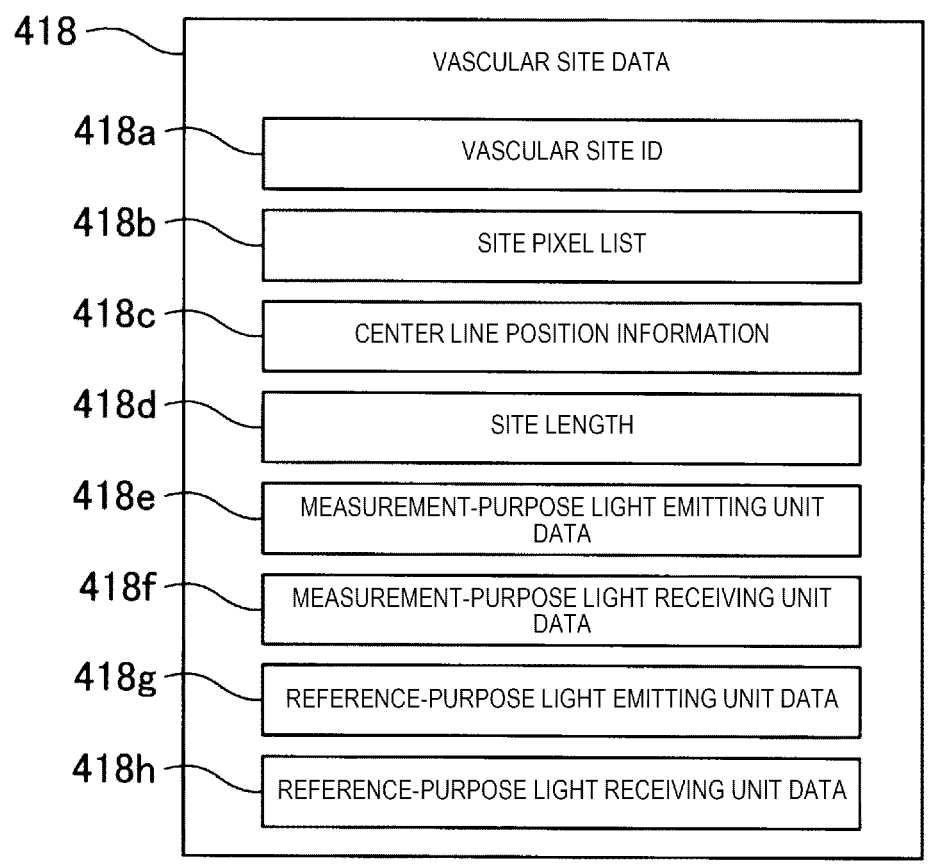

[Fig. 14]
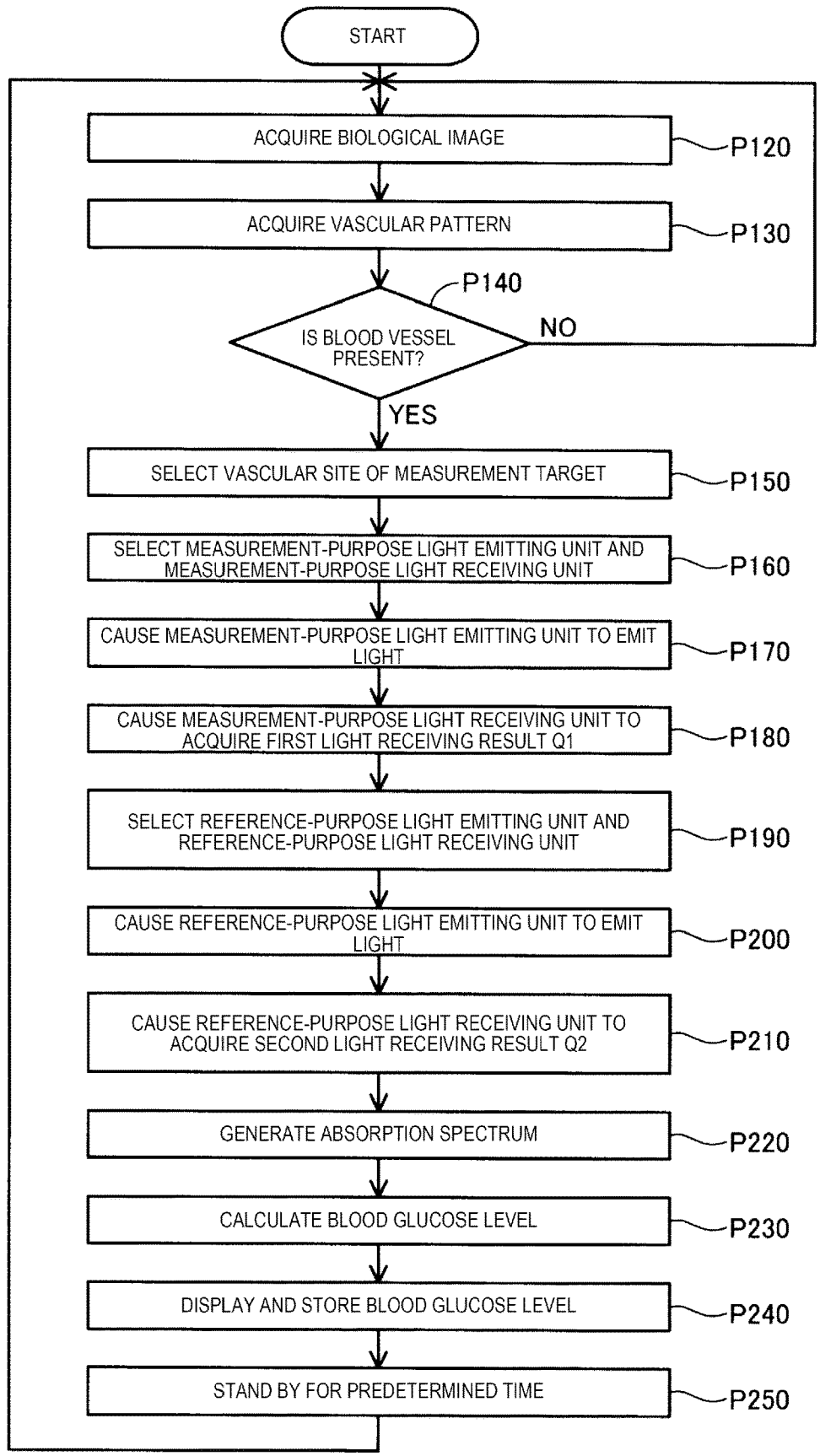

BIOLOGICAL INFORMATION ACQUISITION DEVICE AND BIOLOGICAL INFORMATION ACQUISITION METHOD

TECHNICAL FIELD

The present invention relates to a biological information acquisition device and a biological information acquisition method.

BACKGROUND ART

In the related art, a biological information acquisition device is known which acquires biological information relating to a blood vessel or blood in the blood vessel (for example, refer to PTL 1). PTL 1 discloses a technique for acquiring a blood glucose level of a living body in such a way that (i) a position of the blood vessel is recognized by causing a plurality of light emitting elements to simultaneously emit light in order to recognize where the blood vessel is present inside the living body, and that (ii) the light emitting element located at a specific position is caused to emit the light, based on the position of the blood vessel.

CITATION LIST

Patent Literature

PTL 1: JP-A-2014-124455
PTL 2: JP-A-2007-44491
PTL 3: JP-A-2014-124454

SUMMARY OF INVENTION

Technical Problem

However, according to the technique disclosed in PTL 1, in particular, the plurality of light emitting elements are caused to simultaneously emit the light in order to recognize where the blood vessel is present inside the living body. Consequently, a large amount of energy is required. Accordingly, a technique for realizing energy saving has been demanded. This demand is not limited to a case of searching for the position of the blood vessel. In general, this demand is common to a case of acquiring the biological information.

Solution to Problem

The present invention is made in order to at least partially solve the above-described problem, and can be realized using the following aspects or application examples.

(1) According to a first aspect of the present invention, there is provided a biological information acquisition device. The biological information acquisition device includes a plurality of light emitting elements that irradiate a living body with light, a light receiving unit that receives the light transmitted through the living body, and a control unit that controls the light emitting elements and the light receiving unit, that acquires first biological information by causing the light receiving unit to receive the light emitted by at least one light emitting element in the plurality of light emitting elements, and that acquires second biological information which is different from the first biological information by causing the light receiving unit to receive the light emitted by at least one light emitting element in the plurality of light emitting elements. Light emitting power per unit area of one light emitting element which emits the light when the first biological information is acquired is weaker than light emitting power per unit area of one light emitting element which emits the light when the second biological information is acquired.

According to the biological information acquisition device in the present embodiment, compared to a case where the light emitting power per unit area of one light emitting element emitting the light when the first biological information is acquired is set to be the same as the light emitting power per unit area of one light emitting element emitting the light when the second biological information is acquired, it is possible to minimize the light emitting power per unit area of one light emitting element when the first biological information is acquired. Therefore, energy saving can be realized.

(2) According to another aspect of the present invention, there is provided a biological information acquisition device. The biological information acquisition device includes a plurality of light emitting elements that irradiate a living body with light, a light receiving unit that receives the light transmitted through the living body, and a control unit that controls the light emitting elements and the light receiving unit, that acquires first biological information by causing the light receiving unit to receive the light emitted by at least one light emitting element in the plurality of light emitting elements, and that acquires second biological information which is different from the first biological information by causing the light receiving unit to receive the light emitted by at least one light emitting element in the plurality of light emitting elements. Power density per one light emitting element which emits the light when the first biological information is acquired is weaker than power density per one light emitting element which emits the light when the second biological information is acquired.

According to the biological information acquisition device in the present embodiment, compared to a case where the power density of one light emitting element emitting the light when the first biological information is acquired is set to be the same as the power density of one light emitting element emitting the light when the second biological information is acquired, it is possible to minimize the power density of one light emitting element when the first biological information is acquired. Therefore, energy saving can be realized.

(3) In the above-described biological information acquisition device, current density per one light emitting element which emits the light when the first biological information is acquired may be lower than current density per one light emitting element which emits the light when the second biological information is acquired.

According to the biological information acquisition device in the present embodiment, compared to a case where the current density of one light emitting element emitting the light when the first biological information is acquired is set to be the same as the current density of one light emitting element emitting the light when the second biological information is acquired, it is possible to minimize the current density of one light emitting element when the first biological information is acquired. Therefore, energy saving can be realized.

(4) According to still another aspect of the present invention, there is provided a biological information acquisition device. The biological information acquisition device includes a plurality of light emitting elements that irradiate a living body with light, a light receiving unit that receives the light transmitted through the living body, and a control unit that controls the light emitting elements and the light receiving unit, that acquires first biological information by causing the light receiving unit to receive the light emitted by at least one light emitting element in the plurality of light emitting elements, and that acquires second biological information which is different from the first biological information by causing the light receiving unit to receive the light emitted by at least one light emitting element in the plurality of light emitting elements. Light emitting power when the first biological information is acquired in a first light emitting region which is an inner region of a smallest circle circumscribed by the light emitting elements simultaneously emitting the light when the first biological information is acquired is weaker than light emitting power when the second biological information is acquired in a second light emitting region which is smaller than the first light emitting region and which is an inner region of a smallest circle circumscribed by the light emitting elements simultaneously emitting the light when the second biological information is acquired.

According to the biological information acquisition device in the present embodiment, compared to a case where the light emitting power required when the first biological information is acquired in the first light emitting region is set to be the same as the light emitting power required when the second biological information is acquired in the second light emitting region, it is possible to minimize the light emitting power of one light emitting element when the first biological information is acquired in the first light emitting region. Therefore, energy saving can be realized.

(5) According to still another aspect of the present invention, there is provided a biological information acquisition device. The biological information acquisition device includes a plurality of light emitting elements that irradiate a living body with light, a light receiving unit that receives the light transmitted through the living body, and a control unit that controls the light emitting elements and the light receiving unit, that acquires first biological information by causing the light receiving unit to receive the light emitted by at least one light emitting element in the plurality of light emitting elements, and that acquires second biological information which is different from the first biological information by causing the light receiving unit to receive the light emitted by at least one light emitting element in the plurality of light emitting elements. Power consumption of the light emitting element when the first biological information is acquired in a first light emitting region which is an inner region of a smallest circle circumscribed by the light emitting elements simultaneously emitting the light when the first biological information is acquired is lower than power consumption of the light emitting element when the second biological information is acquired in a second light emitting region which is smaller than the first light emitting region and which is an inner region of a smallest circle circumscribed by the light emitting elements simultaneously emitting the light when the second biological information is acquired.

According to the biological information acquisition device in the present embodiment, compared to a case where the power consumption of the light emitting element when the first biological information is acquired in the first light emitting region is set to be the same as the power consumption of the light emitting element when the second biological information is acquired in the second light emitting region, it is possible to minimize the power consumption of the light emitting element when the first biological information is acquired in the first light emitting region. Therefore, energy saving can be realized.

(6) In the above-described biological information acquisition device, a current flowing in the light emitting element inside the first light emitting region when the first biological information is acquired may be lower than a current flowing in the light emitting element inside the second light emitting region when the second biological information is acquired.

According to the biological information acquisition device in the present embodiment, compared to a case where the current flowing in the light emitting element inside the first light emitting region when the first biological information is acquired is set to be the same as the current flowing in the light emitting element inside the second light emitting region when the second biological information is acquired, it is possible to minimize the current flowing in the light emitting element inside the first light emitting region when the first biological information is acquired. Therefore, energy saving can be realized.

(7) In the above-described biological information acquisition device, the second biological information may include vascular information of the living body.

According to the biological information acquisition device in the present embodiment, the vascular information of the living body can be acquired as the second biological information.

(8) In the above-described biological information acquisition device, the first biological information may include information for specifying a vascular position of the living body.

According to the biological information acquisition device in the present embodiment, information for specifying the vascular position of the living body can be acquired as the first biological information.

(9) In the above-described biological information acquisition device, the light emitting power per unit area of the light emitting element whose light emitting power per unit area is strongest when the first biological information is acquired in the light emitting elements emitting the light when the first biological information is acquired may be weaker than the light emitting power per unit area of the light emitting element whose light emitting power per unit area is weakest when the second biological information is acquired in the light emitting elements emitting the light when the second biological information is acquired.

According to the biological information acquisition device in the present embodiment, compared to a case where the light emitting power per unit area of the light emitting element whose light emitting power per unit area is strongest when the first biological information is acquired in the light emitting elements emitting the light when the first biological information is acquired is set to be the same as the light emitting power per unit area of the light emitting element whose light emitting power per unit area is weakest when the second biological information is acquired in the light emitting elements emitting the light when the second biological information is acquired, it is possible to minimize the light emitting power per unit area when the first biological information is acquired. Therefore, energy saving can be realized.

(10) In the above-described biological information acquisition device, the power density of the light emitting element whose power density is highest when the first biological information is acquired in the light emitting elements emitting the light when the first biological information is acquired may be lower than the power density of the light emitting element whose power density is lowest when the second biological information is acquired in the light emitting elements emitting the light when the second biological information is acquired.

According to the biological information acquisition device in the present embodiment, compared to a case where the power density of the light emitting element whose power density is highest when the first biological information is acquired in the light emitting elements emitting the light when the first biological information is acquired is set to be the same as the power density of the light emitting element whose power density is lowest when the second biological information is acquired in the light emitting elements emitting the light when the second biological information is acquired, it is possible to minimize the power density of the light emitting element when the first biological information is acquired. Therefore, energy saving can be realized.

(11) In the above-described biological information acquisition device, the current density of the light emitting element whose current density is highest when the first biological information is acquired in the light emitting elements emitting the light when the first biological information is acquired may be lower than the current density of the light emitting element whose current density is lowest when the second biological information is acquired in the light emitting elements emitting the light when the second biological information is acquired.

According to the biological information acquisition device in the present embodiment, compared to a case where the current density of the light emitting element whose current density is highest when the first biological information is acquired in the light emitting elements emitting the light when the first biological information is acquired is set to be the same as the current density of the light emitting element whose current density is lowest when the second biological information is acquired in the light emitting elements emitting the light when the second biological information is acquired, it is possible to minimize the current density of the light emitting element when the first biological information is acquired. Therefore, energy saving can be realized.

(12) The above-described biological information acquisition device may further include a battery that supplies energy to the light emitting element so as to emit the light.

According to the biological information acquisition device in the present embodiment, it is possible to provide the battery.

(13) The above-described biological information acquisition device may further include a fixing band for wearing the biological information acquisition device on a wrist of the living body.

According to the biological information acquisition device in the present embodiment, it is possible to provide the fixing band.

(14) In the above-described biological information acquisition device, an OLED may be used as the light emitting element.

According to the biological information acquisition device in the present embodiment, it is possible to use the OLED.

(15) In the above-described biological information acquisition device, the second biological information may be glucose concentration in blood of the living body or oxygen saturation in the blood of the living body.

According to the biological information acquisition device in the present embodiment, the glucose concentration in the blood of the living body or the oxygen saturation in the blood of the living body can be acquired as the second biological information.

The present invention can also be realized using various aspects other than the above-described aspects. For example, the present invention can be realized using aspects such as a biological information acquisition method of acquiring the biological information by using the biological information acquisition device including the plurality of light emitting elements that irradiate the living body with the light and the light receiving unit that receives the light transmitted through the living body, and a computer program for realizing this method, and a non-transitory recording medium (non-transitory storage medium) for storing the computer program.

BRIEF DESCRIPTION OF DRAWINGS

FIG. 1 is a schematic view illustrating a configuration of a biological information acquisition device according to a first embodiment.

FIG. 2 is a schematic plan view illustrating a portion of a sensor module.

FIG. 3 is a configuration diagram of the sensor module.

FIG. 4 is a schematic view for describing a state of acquiring vascular position information.

FIG. 5 is a view illustrating an example of a vascular pattern obtained based on a biological image.

FIG. 6 illustrates an example of a vascular site of a measurement target obtained based on the vascular pattern in FIG. 5.

FIG. 7 is a view for describing selection of a light emitting unit and a light receiving unit.

FIG. 8 is a view for describing the light propagation inside a biological tissue.

FIG. 9 is a schematic view illustrating a relationship between the light emitting unit and a light emitting element and a relationship between the light receiving unit and a light receiving element.

FIG. 10 is a view for describing a light irradiation method when the vascular position information is acquired and when blood glucose level information is acquired.

FIG. 11 is a view illustrating an application example for comparing light irradiation conditions with one another.

FIG. 12 is a functional configuration diagram of a blood glucose level measurement device according to the present embodiment.

FIG. 13 is a view illustrating an example of data configuration of vascular site data.

FIG. 14 is a flowchart for describing a flow in a blood glucose level measurement process.

DESCRIPTION OF EMBODIMENTS

A. First Embodiment

A1. Device Configuration:

FIG. 1 is a schematic view illustrating a configuration of a biological information acquisition device 10 according to a first embodiment. The biological information acquisition device 10 is a biological information acquisition device for noninvasively measuring biological information of a user 2 by using light. In the present embodiment, as the biological information, the biological information acquisition device 10 acquires a blood glucose level which is glucose concentration in blood of the user 2. The biological information acquisition device 10 is also called a blood glucose level measurement device 10. The biological information acquisition device 10 is a wristwatch type, and is a wearable device (wearable instrument) configured to include a main body case 12 and a fixing band 14 to be used so that the main body case 12 is fixed to and worn on a wrist or an arm of the user 2.

A touch panel 16 or an operation switch 18 is disposed on a front surface (surface facing outward when worn by the user 2) of the main body case 12. The touch panel 16 or the operation switch 18 is used so that the user 2 can input a measurement start instruction thereto or a measurement result can be displayed on the touch panel 16.

In addition, a communication device 20 for communicating with an external device and a reader/writer 24 of a memory card 22 are disposed on a side surface of the main body case 12. The communication device 20 is realized by a jack for attaching and detaching a wired cable, or by a wireless communication module and an antenna for wireless communication. The memory card 22 is a data rewritable nonvolatile memory such as a flash memory, a ferroelectric random access memory (FeRAM), and a magnetoresistive random access memory (MRAM).

In addition, a sensor module 50 is disposed on a rear surface of the main body case 12 so that the sensor module 50 can be in contact with a skin surface of the user 2. The sensor module 50 is a measurement-purpose device which emits measurement light onto a skin surface of the user 2 and receives the light transmitted through or reflected on a body of the user 2, and is a thin type image sensor internally equipped with a light source.

Furthermore, the main body case 12 is internally equipped with a rechargeable battery 26 and a control board 30. The battery 26 supplies energy to a light emitting element 53 (to be described later) so as to emit the light. As a method for charging the battery 26, a configuration may be adopted in which an electrical contact is disposed on the rear surface side of the main body case 12 and the battery 26 is set in a cradle connected to a domestic power source so as to be charged via the electrical contact by way of the cradle. Alternatively, wireless charging may be employed.

The control board 30 is provided with a central processing unit (CPU), a main memory, a memory for measurement data, a touch panel controller, and a sensor module controller. The main memory is a storage medium which can store a program and initial set data or which can store computed values of the CPU. The main memory is realized by a RAM, a read only memory (ROM), and a flash memory. A configuration may be adopted in which the program and the initial set data are stored in the memory card 22. The memory for measurement data is a storage medium for storing the measurement data, and is realized by a data rewritable nonvolatile memory such as a flash memory, a ferroelectric memory (FeRAM), and a magnetoresistive memory (MRAM). A configuration may be adopted in which the measurement data is stored in the memory card 22.

FIGS. 2 and 3 are configuration diagrams of the sensor module 50. FIG. 2 is a schematic plan view illustrating a portion of the sensor module 50, and FIG. 3 is a schematic sectional view of the sensor module 50. As illustrated in FIG. 2, the sensor module 50 has a plurality of light emitting elements 53 and a plurality of light receiving elements 59 which are respectively and regularly arranged inside a light receiving and emitting region. Here, the light receiving and emitting region includes the plurality of light emitting elements 53 and the plurality of light receiving elements 59.

As illustrated in FIG. 3, the sensor module 50 is an optical sensor configured so that a light emitting layer 52 in which the plurality of light emitting elements 53 are two-dimensionally arranged in a planar fashion, a light blocking layer 54 which selectively blocks the light other than the light directed toward a light receiving layer 58, a spectral layer 56 which selectively transmits near infrared rays, and the light receiving layer 58 in which the plurality of the light receiving elements 59 are two-dimensionally arranged in a planar fashion are stacked one on another. The sensor module 50 is disposed on the rear surface side of the main body case 12 so that the front surface side (surface on the light emitting layer 52 side) faces the skin surface of the user 2.

The light emitting element 53 emits the light to the living body. For example, the light emitting element 53 is realized by a light emitting diode (LED) or an organic light emitting diode (OLED). In the present embodiment, in order to measure a blood glucose level (glucose concentration in the blood), the light emitting element 53 can emit the light including near infrared rays (light having a wavelength of 0.7 μm to 2.5 μm) having subcutaneously transmittance capability. In the present embodiment, the OLED is used as the light emitting element 53.

The light receiving element 59 receives the light transmitted through or reflected on the living body, and outputs an electric signal corresponding to the received light quantity. For example, the light receiving element 59 is realized by an imaging element such as a charge coupled device (CCD) image sensor and a complementary metal oxide semiconductor (CMOS) image sensor. One light receiving element 59 includes a plurality of elements for receiving each wavelength component necessary for calibration.

As illustrated in FIG. 2, the light emitting element 53 and the light receiving element 59 are arranged in a matrix on a plane defined by a common Xs-Ys orthogonal coordinate system. The light emitting element 53 and the light receiving element 59 respectively have the same arrangement interval in Xs and Ys axis directions. However, both of these are arranged so as to be alternate on an Xs-Ys plane. That is, both of these are arranged so that positions of the light emitting element 53 and the light receiving element 59 in the Xs and Ys axis directions are shifted from each other by a predetermined length.

Each arrangement interval between the light emitting element 53 and the light receiving element 59 can be appropriately set. For example, it is preferable to set the arrangement interval to 1 μm to 500 μm. In view of a balance between manufacturing cost and measurement accuracy, the arrangement interval can be set to 50 μm to 200 μm, for example. The light emitting element 53 and the light receiving element 59 may be juxtaposed with each other without being limited to a configuration in which the light emitting element 53 and the light receiving element 59 are stacked on each other.

A2. Measurement Principle (A) Measurement of Blood Glucose Level

A measurement principle of the blood glucose level according to the present embodiment will be described. In order to measure the blood glucose level, the blood glucose level measurement device 10 is fixed to the user 2 with the fixing band 14 so that the sensor module 50 is in close contact with the skin surface of the user 2. Since the sensor module 50 is in close contact with the skin surface, it is possible to restrain factors that lower the measurement accuracy, such as reflection of the measurement light on the skin surface and scattering near the skin surface. Then, the blood vessel inside the biological tissue directly below the sensor module 50 is set as a measurement target. The measurement light is transmitted through the blood vessel, and the light including the transmitted light passing through the blood vessel is received so as to obtain an absorption spectrum. In this manner, the blood glucose level is estimated and calculated.

(A-1) Acquisition of Vascular Position Information

Specifically, first, vascular position (vascular pattern) information viewed from the skin surface is acquired. The acquisition of the vascular position information can be realized in the same way as vein position detection in the known vein authentication technology.

FIG. 4 is a schematic view for describing a state of acquiring the vascular position information. As illustrated in FIG. 4, all of the light emitting elements 53 of the sensor module 50 are caused to simultaneously emit the light so as to irradiate the skin surface of the user 2 with the measurement light. Then, the light receiving element 59 is used, and the light in which the measurement light is transmitted through the biological tissue (transmitted light) or the light reflected on the biological tissue (reflected light) is received, that is, imaged, thereby acquiring a biological image. When the vascular position information is acquired, only some of the light emitting elements 53 of the sensor module 50 may be caused to emit the light.

The blood vessel is more likely to absorb near infrared rays compared to a non-blood vessel portion. Thus, in the acquired biological image, the blood vessel portion has lower luminance, and is darker than the non-blood vessel portion. Therefore, a portion having the lower luminance is extracted from the biological image. In this manner, the vascular position can be extracted. That is, it is determined whether or not the luminance of each pixel configuring the biological image is equal to or smaller than a predetermined threshold. In this manner, it is possible to determine whether or not the blood vessel exists directly below the corresponding light receiving element 59, that is, it is possible to acquire the vascular position.

FIG. 5 is a view illustrating an example of a vascular pattern P4 obtained based on the biological image. The vascular pattern P4 is information indicating whether a portion is the blood vessel or a non-vascular site for each pixel configuring the biological image, that is, for each position of the light receiving elements 59. In FIG. 5, a hatched band-like portion is a blood vessel 4, and other white outlined portions are extracted as a non-vascular site 8.

(A-2) Selection of Vascular Site as Measurement Target

If the vascular position information is acquired, the blood vessel (more specifically, the vascular site) serving as a measurement target is subsequently selected. The vascular site serving as the measurement target is selected so as to satisfy the following selection condition. The selection condition is that "the vascular site is a bifurcated portion or joined portion of the blood vessel and a portion other than an image end portion, and that the vascular site has a predetermined length and a predetermined width in a longitudinal direction of the blood vessel".

There is a possibility that the light passing through the blood vessel other than the measurement target may be mixed with the received light in a bifurcated/joined site 5*a* (refer to FIG. 5) of the blood vessel. The light transmitted through the blood vessel other than the vascular site serving as the measurement target affects an absorption spectrum of the vascular site serving as the measurement target, thereby causing a possibility that measurement accuracy may become poor. Therefore, the vascular site serving as the measurement target is selected from a portion of the blood vessel other than the bifurcated/joined site 5*a* of the blood vessel.

In an image end portion 5*b* (refer to FIG. 5) of the living body, a bifurcated or joined structure of the blood vessel in the vicinity of the outside of the image is unknown. Accordingly, there is a possibility that the measurement accuracy may become poor due to the same reason as described above. In order to avoid this possibility, the vascular site serving as the measurement target is selected from the portion of the blood vessel other than the image end portion 5*b*.

The light emitted from the light emitting element 53 is diffused and reflected inside the biological tissue, and the light is partially received by the light receiving element 59. In other words, the light partially received by the light receiving element 59 becomes the light transmitted through the blood vessel serving as the measurement target. As a proportion of the transmitted light becomes higher, the transmitted light can become an absorption spectrum which more remarkably shows the characteristics of the components contained in the blood of the blood vessel serving as the measurement target. That is, the measurement accuracy is improved.

The blood vessel which is relatively thinly imaged (short blood vessel in the width direction) is the blood vessel which is inherently thin, or is the blood vessel which is located at a relatively deep position. In this blood vessel, the light quantity of the transmitted light decreases, and the measurement accuracy may become poor. Therefore, the vascular site serving as the measurement target is selected from the portion of the blood vessel (that is, a vascular site having a predetermined width) excluding the blood vessel which is thinly imaged.

FIG. 6 is an example of a vascular site 6 serving as the measurement target obtained based on the vascular pattern P4 in FIG. 5. In FIG. 6, an obliquely hatched portion of the blood vessel 4 is the vascular site 6 selected as the measurement target.

(A-3) Selection of Light Emitting Unit and Light Receiving Unit

Subsequently, a light emitting unit L and a light receiving unit S are selected.

FIG. 7 is a view for describing selection between the light emitting unit L and the light receiving unit S. The light emitting unit L and the light receiving unit S are selected based on the vascular position. In the present embodiment, (i) the light emitting unit L located above the blood vessel is selected as a measurement-purpose light emitting unit Ld, and (ii) the light receiving unit S separated from the measurement-purpose light emitting unit Ld by a predetermined distance W and located above the blood vessel is selected as a measurement-purpose light receiving unit Sd. Here, the term of "above the blood vessel" means that these are located above the vascular site 6 serving as the measurement target.

In addition, (iii) the light emitting unit L which is not located above the blood vessel is selected as a reference-purpose light emitting unit Lr, and (iv) the light receiving unit S which is separated from the reference-purpose light emitting unit Lr by the predetermined distance W and is not located above the blood vessel is selected as a reference-purpose light receiving unit Sr. Here, the term of "not located above the blood vessel" means that these are not located above the blood vessel 4 including the vascular site serving as the measurement target. The predetermined distance W is determined as follows.

FIG. 8 is a view for describing light propagation inside the biological tissue, and illustrates a sectional view taken along the depth direction. The light emitted from one of the light emitting units L is diffused and reflected inside the biological tissue, and the emitted light partially reaches the light receiving unit S. A propagation path of the light forms a so-called banana shape (region interposed between two arcs). The width in the depth direction is most widened in the vicinity of substantially the center, and the entire depth (reachable depth) is deepened in accordance with an interval between the light emitting element 53 and the light receiving element 59.

In order to improve the measurement accuracy, it is desirable that the more light transmitted through the blood vessel 4 is received by the light receiving unit S. From this viewpoint, it is preferable that the blood vessel 4 serving as the target is located below the light emitting unit L and the light receiving unit S. The predetermined distance W is determined in accordance with an assumed depth D of the blood vessel 4 serving as the target. The predetermined distance W, that is, the optimum interval W between the light emitting unit L and the light receiving unit S represents a distance approximately twice the depth D from the skin surface of the blood vessel 4. For example, if the depth D is approximately 3 mm, the optimum distance W is approximately 5 to 6 mm. Next, a relationship between the light emitting unit L and the light emitting element 53, and a relationship between the light receiving unit S and the light receiving element 59 will be described.

FIG. 9 is a schematic view illustrating a relationship between the light emitting unit L and the light emitting element 53, and a relationship between the light receiving unit S and the light receiving element 59. The light emitting unit L in the present embodiment is formed to include the plurality of light emitting elements 53 inside a light emitting region RL.

FIG. 9 illustrates a second light emitting region RL2. The first light emitting region will be described later. In FIG. 9, the second light emitting region RL2 is a region where the light emitting elements 53 are respectively provided three by three in a vertical direction (Ys-direction) and a horizontal direction (Xs-direction).

In the present embodiment, the sensor module 50 includes the light emitting elements 53, the number of which is more than the number of the light emitting elements 53 included inside the second light emitting region RL2. Therefore, the plurality of light emitting units L are present in the light receiving and emitting region of the sensor module 50. Then, a measurement-purpose light emitting unit Ld or a reference-purpose light emitting unit Lr is selected from the plurality of light emitting units L. A region including the plurality of light emitting elements 53 which are caused to emit the light as the measurement-purpose light emitting unit Ld will be referred to as a first light emitting region, and a region including the plurality of light emitting elements 53 which are caused to emit the light as the reference-purpose light emitting unit Lr will be referred to as a second light emitting region.

Similarly, the light receiving unit S in the present embodiment is formed to include the plurality of light receiving elements 59 inside a light receiving region R2. The light receiving region R2 is a partial region of the light receiving and emitting region of the sensor module 50, and means a region having a prescribed shape and size. In the present embodiment, the "light receiving region" will be referred to as an inner region of a smallest circle circumscribed by the light receiving elements 59 simultaneously receiving the light. In FIG. 9, in the light receiving region R2, the three light receiving elements 59 are provided in the vertical direction (Ys-direction), and the three light receiving elements 59 are provided in the horizontal direction (Xs-direction). In this manner, all of the light receiving elements 59 inside the light receiving region R2 are set to receive the light as the light receiving unit S.

In the present embodiment, the sensor module 50 includes the light receiving elements 59, the number of which is more than the number of light receiving elements 59 included in the light receiving region R2. Therefore, the plurality of light receiving units S are present in the light receiving and emitting region of the sensor module 50. Then, a measurement-purpose light receiving unit Sd or a reference-purpose light receiving unit Sr is selected from the plurality of light receiving units S. A region including the plurality of light receiving elements 59 which are caused to receive the light as the measurement-purpose light receiving unit Sd will be referred to as a first light receiving region, and a region including the plurality of light receiving elements 59 which are caused to receive the light as the reference-purpose light receiving unit Sr will be referred to as a second light receiving region.

All of the light receiving elements 59 inside the light receiving region R2 may not be caused to receive the light. In the present embodiment, the predetermined distance W between the light emitting unit L and the light receiving unit S means a distance between a centroid of the light emitting region RL and a centroid of the light receiving region R2. These centroids are geometric centroids determined depending on a shape of the region.

In the present embodiment, a straight line L1 connecting the measurement-purpose light emitting unit Ld and the measurement-purpose light receiving unit Sd to each other and a straight line L2 connecting the reference-purpose light emitting unit Lr and the reference-purpose light receiving unit Sr are substantially parallel to each other. The term of "substantially parallel" means that an angle formed between the two straight lines L1 and L2 falls within 10°. In addition, it is preferable that a distance J between the measurement-purpose light emitting unit Ld and the reference-purpose light emitting unit Lr is 6 mm or shorter. In the present embodiment, the distance J is set to 5 mm.

(A-4) Acquisition of Blood Glucose Level Information

If the measurement-purpose light emitting unit Ld, the measurement-purpose light receiving unit Sd, the reference-purpose light emitting unit Lr, and the reference-purpose light receiving unit Sr are selected for the vascular site 6 serving as the measurement target, the blood glucose level information is acquired. Specifically, first, the measurement-purpose light emitting unit Ld is caused to emit the light so as to acquire a light receiving result Q1 (referred to as a "first light receiving result Q1") of the light from the measurement-purpose light receiving unit Sd. Next, the reference-purpose light emitting unit Lr is caused to emit the light so as to acquire a light receiving result Q2 (referred to as a "second light receiving result Q2") of the light from the reference-purpose light receiving unit Sr. Then, an absorption spectrum is generated using the light receiving result Q1 and the light receiving result Q2. Subsequently, based on the absorption spectrum, the blood glucose level information is acquired using a calibration curve showing a relationship between a predetermined blood glucose level (glucose concentration in the blood) and absorbance. A technique itself for calculating the concentration of a predetermined component (glucose in the present embodiment) from this absorption spectrum is known. In the present embodiment, the known technique can be applied.

(A-5) Light Irradiation Method when Vascular Position Information is Acquired and when Blood Glucose Level Information is Acquired FIG. 10 is a view for describing a light irradiation method when the vascular position information is acquired and when the blood glucose level information is acquired. FIG. 10 illustrates (i) a light emitting state of the sensor module 50 when the vascular position information is acquired and (ii) a light emitting state of the sensor module 50 when the blood glucose level information is acquired. FIG. 10 illustrates that the hatched light emitting element 53 emits the light, and illustrates that the light irradiation amount increases as the hatching is darker. In order to specify which light emitting element emits the light, the sensor module 50 may be imaged using a camera having sensitivity in an infrared region. In this case, it is possible to specify the light emitting element 53 which emits the light.

A first light emitting region RL1 illustrating the light emitting state of the sensor module 50 when the vascular position information is acquired is an inner region of a smallest circle circumscribed by the light emitting elements 53 simultaneously emitting the light when the vascular position information is acquired. In the present embodiment, when the vascular position information is acquired, all of the light emitting elements 53 simultaneously emit the light. Therefore, the first light emitting region RL1 is the inner region of the smallest circle circumscribed by all of the light emitting elements 53.

A second light emitting region RL2 illustrating the light emitting state of the sensor module 50 when the blood glucose level information is acquired is an inner region of a smallest circle circumscribed by the light emitting elements 53 simultaneously emitting the light when the blood glucose level information is acquired. In the present embodiment, when the blood glucose level information is acquired, a total nine (three in the vertical direction and three in the horizontal direction) light emitting elements 53 emit the light. Therefore, the second light emitting region RL2 is the inner region of the smallest circle circumscribed by these nine light emitting elements 53.

In the present embodiment, when the vascular position information is acquired, all of the light emitting elements 53 of the sensor module 50 simultaneously emit the light, and light emitting power per unit area per one light emitting element 53 is 5 mW/cm$^2$. On the other hand, in the present embodiment, when the blood glucose level information is acquired, only some (here, nine) light emitting elements of the sensor module 50 emit the light, and light emitting power per unit area per one light emitting element 53 emitting the light is 34 mW/cm$^2$. That is, in the present embodiment, the light emitting power per unit area per one light emitting element 53 emitting the light when the vascular position information is acquired is weaker than the light emitting power per unit area per one light emitting element 53 emitting the light when the blood glucose level information is acquired. Specifically, the light emitting power per unit area per one of the light emitting elements 53 simultaneously emitting the light when the vascular position information is acquired approximately 1/7 of the light emitting power per unit area per one of the light emitting elements 53 simultaneously emitting the light when the blood glucose level information is acquired. The light emitting power can be measured using a power meter. For example, as the power meter, it is possible to use a power meter having Si having sensitivity from visible light to approximately 1000 nm or a photoelectric conversion unit of InGaS having sensitivity from approximately 800 to approximately 1700 nm.

In general, depending on measurement accuracy and the biological information to be acquired, the required light irradiation amount varies. For example, in a case where the vascular position information is acquired, hemoglobin having a high light absorption rate in blood components is selected as the measurement target. In this case, there is no need to distinguish the hemoglobin between oxidized hemoglobin and reduced hemoglobin. Accordingly, it is possible to relatively easily receive the light. Therefore, the vascular position can be acquired even using a relatively small amount of the light.

On the other hand, when the blood glucose level information is acquired, that is, when information on a substance contained only in a trace amount in the blood such as glucose is acquired, a few signals are obtained by optical measurement. Therefore, a large amount of the light is required for the measurement.

In the present embodiment, the light emitting power per unit area of one light emitting element 53 emitting the light when the vascular position information is acquired is weaker than the light emitting power per unit area per unit of one light emitting element 53 emitting the light when the blood glucose level information is acquired. Therefore, it is possible to restrain wasteful energy consumption without degrading the accuracy of the vascular position information or the blood glucose level information. Accordingly, energy saving can be achieved as the biological information acquisition device 10. As a result, capacity of the battery 26 can be reduced. Therefore, the biological information acquisition device 10 can be miniaturized in size and weight.

In addition, the light emitting power (mW/cm$^2$) per unit area is substantially proportional to the current density (mA/cm$^2$) applied to the light emitting element 53. In the present embodiment, the current density applied per one light emitting element 53 emitting the light when the vascular position information is acquired is 100 mA/cm$^2$. On the other hand, in the present embodiment, the current density applied per one light emitting element 53 emitting the light when the blood glucose level information is acquired is 700 mA/cm$^2$. That is, in the present embodiment, the current density applied per one light emitting element 53 emitting the light when the vascular position information is acquired is lower than the current density applied per one light emitting element 53 emitting the light when the blood glucose level information is acquired.

FIG. 11 is a view illustrating an application example for comparing light irradiation conditions when the vascular position information is acquired and when the blood glucose level information is acquired. As the light irradiation conditions, FIG. 11 illustrates (i) a net light emitting area, (ii) the current density, (iii) an applied current, (iv) a drive voltage, (v) the power consumption, (vi) power density, (vii) the light emitting power per unit area, (viii) the light emitting power, (iv) a light emitting area inside a circumscribed circle, and (v) the light emitting power per a light emitting region. FIG. 11 further illustrates a surface temperature of the sensor module 50 after the irradiation is performed under the light irradiation conditions. The present embodiment corresponds to Application Example 1, and FIG. 11 additionally illustrates Application Examples 2 to 4 and a comparative example.

In the present embodiment, the net light emitting area which is the light emitting area of the light emitting element 53 emitting the light when the vascular position information is acquired is 1.2 cm$^2$ (refer to Application Example 1). On the other hand, the net light emitting area which is the light emitting area of the light emitting element 53 emitting the light when the blood glucose level information is acquired is 0.012 cm$^2$. That is, the light emitting area when the vascular position information is acquired is larger than the light emitting area when the blood glucose level information is acquired. The light emitting area when the vascular position information is acquired is 100 times the light emitting area when the blood glucose level information is acquired. FIG. 10 illustrates scales different from actual scale from a viewpoint of facilitating the understanding of the content.

Therefore, in a case where the light emitting power per unit area of one light emitting element 53 emitting the light when the vascular position information is acquired is set to be the same as the light emitting power per unit area of one light emitting element 53 emitting the light when the blood glucose level information is acquired, a result is obtained as in a comparative example in FIG. 11. That is, the power consumption when the vascular position information is acquired increases as much as 5460 mW, and the surface temperature of the sensor module 50 is higher than 100° C.

In general, heat generated when the light is emitted from a light source depends on the power input. The generated heat is transferred from the sensor module 50 to the main body case 12, and finally reaches a human body wearing the biological information acquisition device 10. Therefore, if the temperature of the sensor module 50 rises up to the temperature illustrated in the comparative example, it may be dangerous to the human body wearing the biological information acquisition device 10. In addition, even if the temperature of the sensor module 50 does not rise beyond 100° C., if the temperature of the biological information acquisition device 10 is not maintained at prescribed temperature or lower, in a case where the biological information acquisition device 10 is used in a state where the biological information acquisition device 10 is brought into contact with the human body for a long period of time, there is a possibility of a low-temperature burn. Therefore, controlling the light emitting power is particularly important in a case where the light emitting elements 53 in a wide range are caused to emit the light when the vascular position information is acquired.

The light emitting area inside the circumscribed circle serving as the area of the first light emitting region RL1 which is the inner region of the smallest circle circumscribed by the light emitting elements 53 simultaneously emitting the light when the vascular position information is acquired is approximately 1.9 cm$^2$ unlike the above-described net light emitting area (refer to Application Example 1). On the other hand, the light emitting area serving as the area of the second light emitting region RL2 which is the inner region of the smallest circle circumscribed by the light emitting elements 53 simultaneously emitting the light when the blood glucose level information is acquired is approximately 0.019 cm$^2$. Therefore, the light emitting power per the first light emitting region RL1 is approximately 3.2 mW/cm$^2$, and the light emitting power per the second light emitting region RL2 is approximately 22 mW/cm$^2$.

In addition, in the biological information acquisition device 10 according to the present embodiment, the OLED is used as the light emitting element 53. Glass transition temperature of an organic material used for the OLED is generally from approximately 90° C. to 130° C. However, there is a possibility that the temperature of the OLED may reach the glass transition temperature due to the heat generated by emitting the light. Then, in a case where the temperature of the OLED reaches the glass transition temperature, light emitting efficiency of the OLED may be lowered. However, in the present embodiment, the light emitting power of the light emitting element 53 is properly controlled. In this manner, it is possible to restrain the light emitting element 53 from being degraded. Therefore, the OLED can be used.

(A-6) Description of Other Techniques

When the absorption spectrum is generated, for example, a wavelength of the light to be emitted is changed by the light emitting unit L. In this manner, a wavelength λ of the light emitted to the skin surface is changed within a near infrared region, and transmittance of the vascular site 6 is obtained for each wavelength λ. The transmittance T(λ) is obtained as T(λ)=Os(λ)/Or(λ), based on light intensity Os(λ) obtained by the measurement-purpose light receiving unit Sd and light intensity Or(λ) obtained by the reference-purpose light receiving unit Sr. Then, absorbance is obtained from the transmittance so as to generate the absorption spectrum.

Here, a calculation principle of the transmittance will be briefly described. In general, if the intensity of the light emitted by the light emitting unit L is set to P(λ), the transmittance of an object portion through which the emitted light is transmitted is set to T(λ), and sensitivity determined in the light receiving unit S is set to S(λ), the light intensity O(λ) obtained by the light receiving unit S is expressed by O(λ)=P(λ)·T(λ)·S(λ).

Based on this relational expression, the light intensity Or(λ) obtained by the reference-purpose light receiving unit Sr which does not include the transmitted light of the blood vessel 4 is obtained as Or(λ)=P(λ)·S(λ), if the transmittance T(λ) of the non-vascular site portion is assumed as "1".

In addition, the light intensity Os(λ) obtained by the measurement-purpose light receiving unit Sd which includes the transmitted light of the blood vessel 4 is expressed by Os(λ)=P(λ)·T(λ)·S(λ). Based on these two expressions, the transmittance T(λ) is obtained. In addition, the transmittance T(λ) is a value relative to the transmittance of the non-vascular site 8.

A3. Functional Configuration

FIG. 12 is a functional configuration diagram of the blood glucose level measurement device 10 according to the present embodiment. The blood glucose level measurement device 10 is configured to functionally include an operation input unit 110, a display unit 120, a sound output unit 130, a communication unit 140, an irradiation unit 210, an imaging unit 220, a control unit 300, and a storage unit 400.

The operation input unit 110 is an input device such as a button switch, a touch panel, and various sensors, and outputs an operation signal according to the operation to the control unit 300. The operation input unit 110 performs various instruction inputs such as instructions to start measurement of the blood glucose level. In FIG. 1, the operation switch 18 or the touch panel 16 corresponds to the operation input unit 110.

The display unit 120 is a display device such as a liquid crystal display (LCD), and performs various displays based on a display signal output from the control unit 300. The measurement result is displayed on the display unit 120. In FIG. 1, the touch panel 16 corresponds to the display unit 120.

The sound output unit 130 is a sound output device such as a speaker, and performs various sound outputs based on a sound signal output from the control unit 300. The sound output unit 130 outputs a notification sound for notifying the measurement start or the measurement completion of the blood glucose level, and occurrence of a low blood glucose level.

The communication unit 140 is a communication device such as a wireless communication device, a modem, a jack of a communication cable for wired communication, and a control circuit, and external communication is realized by being connected to a communication line. In FIG. 1, the communication device 20 corresponds to the communication unit 140.

The irradiation unit 210 has multiple light emitting elements 53 which are two-dimensionally arranged in a planar fashion. The light emitting layer 52 of the sensor module 50 illustrated in FIG. 2 corresponds to the irradiation unit 210. The arrangement position of the irradiation unit 210 (specifically, position coordinates of the respective light emitting elements 53 in the Xs-Ys orthogonal coordinate system) is stored as a light emitting element list 406 in the storage unit 400.

The imaging unit 220 has multiple light receiving elements 59 which are two-dimensionally arranged in a planar fashion. The light receiving layer 58 of the sensor module 50 illustrated in FIG. 2 corresponds to the imaging unit 220. The arrangement position of the imaging unit 220 (specifically, position coordinates of the respective light receiving elements 59 in the Xs-Yx orthogonal coordinate system) is stored as a light receiving element list 408 in the storage unit 400.

For example, the control unit 300 is realized by a microprocessor such as a CPU or a graphics processing unit (GPU) or electronic components such as an application specific integrated circuit (ASIC) and an IC memory. Based on a predetermined program, data, or an operation signal output from the operation input unit 110, the control unit 300 performs various arithmetic processes, and controls the operation of the blood glucose level measurement device 10. In FIG. 1, the control board 30 corresponds to the control unit 300. In addition, the control unit 300 has a blood glucose level measurement unit 310, an irradiation control unit 342, and an imaging control unit 344. The irradiation control unit 342 selectively controls each of the plurality of light emitting elements 53 to emit the light. The imaging control unit 344 acquires the light quantity received from each of the plurality of the light receiving elements 59.

The blood glucose level measurement unit 310 has a biological image acquisition unit 314, a vascular pattern acquisition unit 316, a vascular site selection unit 318, a measurement-purpose light receiving and emitting unit selection unit 320, a reference-purpose light receiving and emitting unit selection unit 322, an absorption spectrum calculation unit 324, and a component value calculation unit 326. The blood glucose level measurement unit 310 measures the glucose concentration, that is, the blood glucose level in the blood of the user 2.

The biological image acquisition unit 314 acquires a biological image of the user 2. Acquisition of the biological image is realized by appropriately using a biological image capturing technique in the known vein authentication technology. That is, the light emitting elements 53 are caused to simultaneously emit the light, and the light receiving elements 59 measures (images) the light. Then, a luminance image based on the light measurement result, that is, the biological image is generated. The biological image acquired by the biological image acquisition unit 314 is stored as biological image data 414 in the storage unit 400.

The vascular pattern acquisition unit 316 performs predetermined image processing on the biological image acquired by the biological image acquisition unit 314 so as to acquire a vascular pattern. Specifically, the image processing is realized by appropriately using a technique for identifying a vein pattern from the biological image in the known vein authentication technology. For example, reference luminance is compared for each pixel of the biological image, and each pixel is subjected to binary coded processing and filter processing. The pixel whose luminance is lower than the reference luminance indicates the blood vessel, and the pixel whose luminance is equal to or higher than the reference luminance indicates the non-vascular site. The vascular pattern acquired by the vascular pattern acquisition unit 316 is stored as vascular pattern data 416 in the storage unit 400.

Based on the vascular pattern acquired by the vascular pattern acquisition unit 316, the vascular site selection unit 318 selects the vascular site 6 indicating a predetermined selection condition, as the measurement target. Here, the vascular site 6 serving as the measurement target may be one or more. Each of the vascular sites 6 selected as the measurement target is stored as vascular site data 418 in the storage unit 400.

FIG. 13 illustrates an example of a data configuration of the vascular site data 418. The vascular site data 418 stores a vascular site ID 418a serving as identification information of the vascular site, a site pixel list 418b, center line position information 418c, a site length 418d which is a length in the longitudinal direction of the blood vessel, measurement-purpose light emitting unit data 418e, measurement-purpose light receiving unit data 418f, reference-purpose light emitting unit data 418g, and reference-purpose light receiving unit data 418h. The site pixel list 418b is a list of pixels (that is, the light receiving element 59) corresponding to the vascular site. The center line position information 418c is information on the position coordinates of the center line (center in the width direction of the blood vessel and a line extending along the longitudinal direction of the blood vessel) of the vascular site in the Xs-Ys orthogonal coordinate system.

The measurement-purpose light receiving and emitting unit selection unit 320 selects the measurement-purpose light emitting unit Ld and the measurement-purpose light receiving unit Sd for each of the vascular sites 6 serving as the measurement target. Specifically, one position on the center line of the vascular site 6 is selected as the measurement-purpose light emitting unit Ld in the Xs-Ys orthogonal coordinate system (that is, on the skin surface), and the measurement-purpose light receiving unit Sd which is separated from the measurement-purpose light emitting unit Ld by the predetermined distance W and which is located on the center line of the vascular site 6 is selected. A selection condition of the measurement-purpose light emitting unit Ld and the measurement-purpose light receiving unit Sd will be referred to as a first condition. The predetermined distance W is stored as optimum distance data 410 in the storage unit 400. For example, a selection method of one position on the center line of the vascular site 6 is determined using a substantially center position in the longitudinal direction of the vascular site 6. The selected measurement-purpose light emitting unit Ld is stored as measurement-purpose light emitting unit data 418e, and the selected measurement-purpose light receiving unit Sd is stored as measurement-purpose light receiving unit data 418f.

In a case where the measurement-purpose light emitting unit Ld and the measurement-purpose light receiving unit Sd which satisfy the above-described first condition are not present, it is determined whether or not the measurement-purpose light emitting unit Ld and the measurement-purpose light receiving unit Sd which similarly satisfy the above-described first condition are present at a position separated from the one position by a predetermined unit distance along the center line of the vascular site 6. Nevertheless, in a case where the measurement-purpose light emitting unit Ld and the measurement-purpose light receiving unit Sd which satisfy the above-described first condition are not present, this process is similarly repeated. In this manner, the measurement-purpose light emitting unit Ld and the measurement-purpose light receiving unit Sd are searched for and selected. The reference-purpose light emitting unit Lr is stored as the reference-purpose light emitting unit data 418g, and the selected reference-purpose light emitting unit Lr is stored as the reference-purpose light receiving unit data 418h.

Based on the measurement-purpose light emitting unit Ld and the measurement-purpose light receiving unit Sd which are set by the measurement-purpose light receiving and emitting unit selection unit 320, the reference-purpose light receiving and emitting unit selection unit 322 selects one position which is not located above the blood vessel 4, as the reference-purpose light emitting unit Lr, and selects the reference-purpose light receiving unit Sr which is separated from the reference-purpose light emitting unit Lr by the predetermined distance W and which is not located above the blood vessel 4. A selection condition of the reference-purpose light emitting unit Lr and the reference-purpose light receiving unit Sr will be referred to as a second condition.

In the present embodiment, as illustrated in FIG. 7, the reference-purpose light receiving unit Sr is selected in which the distance J between the measurement-purpose light emitting unit Ld and the reference-purpose light emitting unit Lr is mm, and in which the straight line connecting the measurement-purpose light emitting unit Ld and the measurement-purpose light receiving unit Sd to each other and the straight line connecting the reference-purpose light emitting unit Lr and the reference-purpose light receiving unit Sr to each other are substantially parallel to each other. The above-described selection condition different from the first condition and the second condition will be referred to as a third selection condition. In a case where the reference-purpose light emitting unit Lr and the reference-purpose light receiving unit Sr which satisfy the second condition and the third condition are not present, the measurement-purpose light receiving and emitting unit selection unit 320 searches for and selects the measurement-purpose light emitting unit Ld and the measurement-purpose light receiving unit Sd.

The absorption spectrum calculation unit 324 generates an absorption spectrum for each of the vascular sites 6 serving as the measurement target. Specifically, based on the first light receiving result Q1 obtained from the measurement-purpose light receiving unit Sd and the second light receiving result Q2 obtained from the reference-purpose light receiving unit Sr, the transmittance T of each wavelength λ is calculated so as to generate the absorption spectrum. Furthermore, in a case where the plurality of vascular sites 6 serving as the measurement target are present, absorption spectra of the plurality of respective vascular sites 6 serving as the measurement targets are averaged so as to calculate an average absorption spectrum. The absorption spectrum calculated by the absorption spectrum calculation unit 324 is stored as absorption spectrum data 420 in the storage unit 400.

Based on the absorption spectrum calculated by the absorption spectrum calculation unit 324, the component value calculation unit 326 calculates the glucose concentration (that is, the blood glucose level) which indicates the blood concentration of a target blood component. In the present embodiment, the absorption spectrum is used for an analysis method such as a multiple regression analysis method, a principal component regression analysis method, a PLS regression analysis method, and an independent component analysis method. In a case where the plurality of vascular sites 6 serving as the measurement target are present, the blood glucose level is calculated from the average absorption spectrum obtained by averaging the absorption spectra of the respective vascular sites 6. The blood glucose levels calculated by the component value calculation unit 326 are accumulated and stored in the storage unit 400 as measured blood glucose level data 422 in association with the measurement time.

The storage unit 400 is a storage device such as a ROM, a RAM, and a hard disk, and stores programs and data for the control unit 300 to integrally control the blood glucose level measurement device 10. The storage unit 400 is used as a work region of the control unit 300, and temporarily stores calculation results obtained by the control unit 300 or operation data output from the operation input unit 110. In FIG. 1, the main memory or the measurement data memory mounted on the control board 30 corresponds to the storage unit 400. The storage unit 400 stores a system program 402, a blood glucose level measurement program 404, a light emitting element list 406, a light receiving element list 408, optimum distance data 410, biological image data 414, vascular pattern data 416, vascular site data 418, absorption spectrum data 420, and measured blood glucose level data 422.

A4. Biological Information Acquisition Method:

FIG. 14 is a flowchart for describing a flow in a blood glucose level measurement process as the biological information acquisition method. The process is realized by the control unit 300 which performs the process according to the blood glucose level measurement program 404.

Referring to FIG. 14, the blood glucose level measurement unit 310 performs a measurement process for measuring the blood glucose level of the user. First, the biological image acquisition unit 314 of the blood glucose level measurement unit 310 sets the entire surface of the light emitting surface of the sensor module 50 (that is, a range including substantially all of the light emitting elements 53) as a light emitting range. The light emitting elements 53 within the light emitting range are caused to emit the light so as to obtain the biological image of the user (Step P120). Subsequently, the vascular pattern acquisition unit 316 acquires the vascular pattern viewed from the skin surface, based on the obtained biological image (Step P130). As a result, if the vascular pattern cannot be obtained (Step P140: NO), the process returns to Step P120.

If the vascular pattern is obtained (Step P140: YES), the vascular site selection unit 318 selects the vascular site serving as the measurement target which satisfies the predetermined selection condition, based on the obtained vascular pattern (Step P150). Then, the measurement-purpose light receiving and emitting unit selection unit 320 selects the measurement-purpose light emitting unit Ld and the measurement-purpose light receiving unit Sd (Step P160). Next, the measurement-purpose light emitting unit Ld is caused to emit the light (Step P170), and the first light receiving result Q1 is obtained by the selected measurement-purpose light receiving unit Sd (Step P180).

Thereafter, the reference-purpose light receiving and emitting unit selection unit 322 selects the reference-purpose light emitting unit Lr and the reference-purpose light receiving unit Sr (Step P190). Next, the reference-purpose light emitting unit Lr is caused to emit the light (Step P200), and the second light receiving result Q2 is obtained by the selected reference-purpose light receiving unit Sr (Step P210). A predetermined time interval is set between the step of acquiring the first light receiving result (Step P180) and the step of acquiring the second light receiving result (Step P210). In the present embodiment, the interval for 5 seconds is set as the predetermined time interval.

Next, the absorption spectrum calculation unit 324 generates the absorption spectrum for the vascular site 6 by using the first light receiving result Q1 and the second light receiving result Q2 (Step P220). Furthermore, in a case where the plurality of vascular sites 6 serving as the measurement target are present, the absorption spectrum obtained by averaging the absorption spectra of the respective vascular sites 6 is calculated.

Thereafter, based on the absorption spectrum, the component value calculation unit 326 calculates the glucose concentration in the blood, that is, the blood glucose level (Step P230). Then, the calculated blood glucose levels are displayed on the display unit 120, and are accumulated and stored in association with the measurement time (Step P240). After a predetermined waiting time elapses (Step P250), the process returns to Step P120, and the subsequent blood glucose level is similarly measured.

A5. Additional Operation Effect

In the biological information acquisition device 10 according to the present embodiment, the measurement-purpose light emitting unit Ld is selected, based on the vascular position. In this manner, the light emitting unit L suitable for acquiring the biological information relating to the blood vessel can be selected as the measurement-purpose light emitting unit Ld. Therefore, according to the biological information acquisition device 10 in the present embodiment, the biological information relating to the blood vessel can be accurately acquired.

In the biological information acquisition device 10 according to the present embodiment, the light source (the measurement-purpose light emitting unit Ld) in the first light receiving result is different from the light source in the second light receiving result. Therefore, it is possible to select the measurement-purpose light emitting unit Ld which is located above the blood vessel, and it is possible to select the reference-purpose light emitting unit Lr which is not located above the blood vessel. As a result, in a case of the first light receiving result obtained by causing the measurement-purpose light receiving unit Sd located above the blood vessel to receive the light emitted from the measurement-purpose light emitting unit Ld located above the blood vessel, the emitted light passes through the blood vessel at a high rate. Accordingly, the first light receiving result includes a lot of information relating to the blood vessel and the blood inside the blood vessel. On the other hand, in a case of the second light receiving result obtained by causing the reference-purpose light receiving unit Sr which is not located above the blood vessel to receive the light emitted from the reference-purpose light emitting unit Lr which is not located above the blood vessel, the emitted light passes through the blood vessel at a low rate. Accordingly, the second light receiving result includes less information relating to the blood vessel or the blood inside the blood vessel. The biological information is acquired using the first light receiving result and the second light receiving result in this way. Therefore, according to the biological information acquisition device 10 in the present embodiment, the biological information can be accurately acquired.

In addition, in the biological information acquisition device 10 according to the present embodiment, the straight line connecting the measurement-purpose light emitting unit Ld and the measurement-purpose light receiving unit Sd to each other and the straight line connecting the reference-purpose light emitting unit Lr and the reference-purpose light receiving unit Sr are substantially parallel to each other. In addition, the distance between the measurement-purpose light emitting unit Ld and the reference-purpose light emitting unit Lr is 6 mm or shorter. Therefore, a structure of the living body in a light path where the light emitted by the measurement-purpose light emitting unit Ld moves forward to the measurement-purpose light receiving unit Sd approximates to a structure of the living body in a light path where the light emitted by the reference-purpose light emitting unit Lr moves forward to the reference-purpose light receiving unit Sr, except that the emitted light does not pass through the vascular site 6. Therefore, according to the biological information acquisition device 10 in the present embodiment, the biological information can be acquired using the first light receiving result and the second light receiving result. Accordingly, the biological information can be accurately acquired.

In addition, in the biological information acquisition device 10 according to the present embodiment, as a partial region of the light receiving and emitting region, the light emitting region RL having a prescribed shape and size is selected, and the plurality of light emitting elements 53 inside the selected light emitting region RL are caused to emit the light as the measurement-purpose light emitting unit Ld or the reference-purpose light emitting unit Lr. In this way, the light emitting unit L according to the present embodiment is formed from the plurality of light emitting elements 53. Therefore, compared to a case where one light emitting unit is formed from one light emitting element, the biological information acquisition device 10 according to the present embodiment can obtain sufficient light emitting intensity. As a result, according to the biological information acquisition device 10 in the present embodiment, the biological information can be accurately acquired.

Similarly, in the biological information acquisition device 10 according to the present embodiment, as a partial region of the light receiving and emitting region, the light receiving region R2 having a prescribed shape and size is selected, and the plurality of light receiving elements 59 inside the selected light receiving region R2 are caused to receive the light as the measurement-purpose light receiving unit Sd or the reference-purpose light receiving unit Sr. In this way, the light receiving unit S according to the present embodiment is formed from the plurality of light receiving elements 59. Therefore, compared to a case where one light receiving unit is formed from one light receiving element, the biological information acquisition device 10 according to the present embodiment can obtain the sufficient light receiving amount. As a result, according to the biological information acquisition device 10 in the present embodiment, the biological information can be accurately acquired.

In addition, in the biological information acquisition device 10 according to the present embodiment, one light emitting unit L is formed from a group of the plurality of smaller light emitting elements 53. Accordingly, a position of the light emitting unit L can be selected in pitch unit of the small light emitting element 53. Therefore, according to the biological information acquisition device 10 in the present embodiment, the light emitting unit L can be more freely selected.

Similarly, in the biological information acquisition device 10 according to the present embodiment, one light receiving unit S is formed from a group of the plurality of smaller light receiving elements 59. Accordingly, a position of the light receiving unit S can be selected in pitch unit of the small light receiving element 59. Therefore, according to the biological information acquisition device 10 in the present embodiment, the light receiving unit S can be more freely selected.

In the biological information acquisition method according to the present embodiment, the predetermined time is set between the step of acquiring the first light receiving result (Step P180 (refer to FIG. 14)) and the step of acquiring the second light receiving result (Step P210). Therefore, it is possible to restrain the reference-purpose light receiving unit Sr from receiving light emitted by the measurement-purpose light emitting unit Ld, or to restrain the measurement-purpose light receiving unit Sd from receiving the light emitted by the reference-purpose light emitting unit Lr. As a result, according to the biological information acquisition method of the present embodiment, the biological information can be accurately acquired.

B. Second Embodiment

The second embodiment is different from the first embodiment in that a selection method of the reference-purpose light emitting unit Lr and the reference-purpose light receiving unit Sr is different. However, the other configurations are the same as those according to the first embodiment.

In a biological information acquisition device 10A according to a second embodiment, a position where the luminance when the biological image is acquired falls within the top 10% inside the whole light receiving and emitting region is selected as the reference-purpose light emitting unit Lr and the reference-purpose light receiving unit Sr. A distance between the reference-purpose light emitting unit Lr and the reference-purpose light receiving unit Sr is set to the predetermined distance W which is the same as that according to the first embodiment.

As described above, the blood vessel is more likely to absorb near infrared rays than the non-blood vessel. Accordingly, in the acquired biological image, the vascular portion has lower luminance than the non-blood vessel. In addition, capillary blood vessels pass through all over the human body. Therefore, there is a high possibility that the blood vessel including the capillary blood vessels may not exist at a position where all ranks of the luminance fall within the top 10% when the biological image is acquired. This position is selected as the reference-purpose light emitting unit Lr and the reference-purpose light receiving unit Sr. In this manner, the second light receiving result obtained by the reference-purpose light receiving unit Sr from the light emitted by the reference-purpose light emitting unit Lr has less information relating to the blood vessel or the blood in the blood vessel. As a result, according to the biological information acquisition device 10 in the present embodiment, the biological information can be accurately acquired.

C. Modification Example

The present invention is not limited to the above-described application examples or modification example, and can be embodied in various aspects within the scope not departing from the gist of the present invention. For example, the following modifications can be adopted.

C1. Modification Example 1

From a viewpoint of energy saving of the biological information acquisition device 10, as the light irradiation conditions when the vascular position information is acquired and when the blood glucose level information is acquired, it is preferable that the conditions have one or more characteristic points described below.

<Characteristic Point 1>

The power density per one of the light emitting elements 53 simultaneously emitting the light when the vascular position information is acquired is lower than the power density per one of the light emitting elements 53 simultaneously emitting the light when the blood glucose level information is acquired.

<Characteristic Point 2>

The current density per one of the light emitting elements 53 simultaneously emitting the light when the vascular position information is acquired is lower than the current density per one of the light emitting elements 53 simultaneously emitting the light when the blood glucose level information is acquired.

<Characteristic Point 3>

The light emitting power (mW) when the vascular position information is acquired in the first light emitting region RL1 which is the inner region of the smallest circle circumscribed by the light emitting elements 53 simultaneously emitting the light when the vascular position information is acquired is weaker than the light emitting power (mW) when the blood glucose level information is acquired in the second light emitting region RL2 which is the inner region of the smallest circle circumscribed by the light emitting elements 53 simultaneously emitting the light when the blood glucose level information is acquired.

<Characteristic Point 4>

The power consumption (mW) of the light emitting element 53 when the vascular position information is acquired in the first light emitting region RL1 which is the inner region of the smallest circle circumscribed by the light emitting elements 53 simultaneously emitting the light when the vascular position information is acquired is lower than the power consumption (mW) of the light emitting element 53 when the blood glucose level information is acquired in the second light emitting region RL2 which is the inner region of the smallest circle circumscribed by the light emitting elements 53 simultaneously emitting the light when the blood glucose level information is acquired.

<Characteristic Point 5>

The applied current (mA) in the first light emitting region RL1 which is the inner region of the smallest circle circumscribed by the light emitting elements 53 simultaneously emitting the light when the vascular position information is acquired is lower than the applied current (mA) in the second light emitting region RL2 which is the inner region of the smallest circle circumscribed by the light emitting elements 53 simultaneously emitting the light when the blood glucose level information is acquired.

<Characteristic Point 6>

The current flowing in the light emitting element 53 inside the first light emitting region RL1 when the vascular position information is acquired is lower than the current flowing in the light emitting element 53 inside the second light emitting region RL2 when the blood glucose level information is acquired.

<Characteristic Point 7>

The light emitting power per unit area of the light emitting element 53 having the strongest light emitting power per unit area when the vascular position information is acquired in the light emitting elements 53 simultaneously emitting the light when the vascular position information is acquired is weaker than the light emitting power per unit area of the light emitting element 53 having the weakest light emitting power per unit area when the blood glucose level information is acquired in the light emitting elements 53 simultaneously emitting the light when the blood glucose level information is acquired.

<Characteristic Point 8>

The power density of the light emitting element 53 having the highest power density when the vascular position information is acquired in the light emitting elements 53 simultaneously emitting the light when the vascular position information is acquired is lower than the power density of the light emitting element 53 having the lowest power density when the blood glucose level information is acquired in the light emitting elements 53 emitting the light when the blood glucose level information is acquired.

<Characteristic Point 9>

The current density of the light emitting element 53 having the highest current density when the vascular position information is acquired in the light emitting elements 53 simultaneously emitting the light when the vascular position information is acquired is lower than the current density of the light emitting element 53 having the lowest current density when the blood glucose level information is acquired in the light emitting elements 53 emitting the light when the blood glucose level information is acquired.

C2. Modification Example 2

In the above-described embodiment, the vascular position information and the blood glucose level information are acquired as the biological information. In other words, the vascular position information which is the information for specifying the vascular position of the living body is acquired as the first biological information. The vascular information of the living body which is different from the first biological information is acquired as the second biological information. However, the present invention is not limited thereto.

For example, instead of the vascular position information, position information of a bone may be acquired as the first biological information. The position information of the bone is acquired, thereby enabling the position of the living body to be specified relative to the biological information acquisition device 10. In addition, for example, oxygen saturation in the blood of the living body of the user may be acquired as the second biological information. In addition, the blood glucose level information and the oxygen saturation information in the blood may be acquired as the second biological information. Furthermore, information other than the blood of the living body may be acquired as the second biological information. For example, the information other than the blood of the living body can include bone density of the living body. The oxygen saturation means a ratio of hemoglobin bound to oxygen in the hemoglobin contained in a red blood cell. In a case of the hemoglobin contained in the blood, absorbance of red light is different from absorbance of infrared light depending on whether or not the hemoglobin is bound to oxygen. Therefore, for example, the oxygen saturation can be acquired by using a plurality of element sets having different light emitting wavelength and light receiving wavelength, such as elements which emit the red light or receive the red light, and elements which emit the infrared light or receive the infrared light.

In addition, according to the above-described embodiment, the present invention is applied to the device for acquiring the blood glucose level. However, the present invention is not limited thereto. For example, the device to which the present invention is applicable includes a human body component analysis device such as a skin diagnosis device, a body fat measurement device, an in-vivo fluorescent light source observation device, a vein authentication device, an infrared scanner device, a skin cancer diagnosis device, a pupil observation device, and a blood vessel observation device. The light emitting unit according to the present invention is applicable to a light source of these devices.

C3. Modification Example 3

In the above-described embodiments, after the light emitting unit L is selected, the light receiving unit S separated from the light emitting unit L by the predetermined distance W is selected. However, the present invention is not limited thereto. After the light receiving unit S is selected, the light emitting unit L separated from the light receiving unit S by the predetermined distance W may be selected. In addition, as the position of the light emitting unit L and the light receiving unit S, it is possible to employ various positions other than the position in the example illustrated in FIG. 7.

C4. Modification Example 4

In the above-described embodiments, after the step of acquiring the first light receiving result Q1 is performed (Step P180), the step of acquiring the second light receiving result Q2 is performed (Step P210). However, the present invention is not limited thereto. After the step of acquiring the second light receiving result Q2, the step of acquiring the first light receiving result Q1 may be performed.

C5. Modification Example 5

In the above-described embodiments, the position which is not located above the blood vessel 4 is selected as the reference-purpose light emitting unit Lr, and the reference-purpose light receiving unit Sr which is separated from the reference-purpose light emitting unit Lr by the predetermined distance W and which is not located above the blood vessel 4 is selected. However, the invention is not limited thereto. That is, in addition to the above-described condition, a condition may be added which does not include the position located above the blood vessel between the reference-purpose light emitting unit Lr and the reference-purpose light receiving unit Sr. In this manner, in a case of the second light receiving result obtained by the reference-purpose light receiving unit Sr, the emitted light passes through the blood vessel at a low rate. Accordingly, the second light receiving result has less information relating to the blood vessel or the blood inside the blood vessel. As a result, the biological information can be accurately acquired.

C6. Modification Example 6

In the above-described embodiments, after the light emitting unit L and the light receiving unit S are selected (for example, Step P160), the light emitting unit L is caused to emit the light (for example, Step P170). However, the present invention is not limited thereto. After the light emitting unit L is caused to emit the light, the light receiving unit S may be selected.

C7. Modification Example 7

In the above-described embodiments, all of the light emitting elements 53 inside the first light emitting region RL1 emit the light when the vascular position information is acquired, the all of light emitting elements 53 inside the second light emitting region RL2 emit the light when the blood glucose level information is acquired. However, the present invention is not limited thereto. That is, in the light emitting elements 53 inside the first light emitting region RL1, at least one of the light emitting elements 53 may emit the light when the vascular position information is acquired. In the light emitting elements 53 inside the second light emitting region RL2, at least one of the light emitting elements 53 may emit the light when the blood glucose level information is acquired.

The elements other than the elements described in the independent claims among the configuration elements in the above-described application examples and modification examples are additional elements, and may be appropriately omitted.

REFERENCE SIGNS LIST

- 2: user
- 4: target blood vessel
- 5*a*: bifurcated/joined site
- 5*b*: end portion
- 5*b*: image end portion
- 6: vascular site
- 8: non-vascular site
- 10, 10A: biological information acquisition device
- 12: main body case
- 14: fixing band
- 16: touch panel
- 18: operation switch
- 20: communication device
- 22: memory card
- 24: reader/writer
- 26: battery
- 30: control board
- 50: sensor module
- 52: light emitting layer
- 53: light emitting element
- 54: light blocking layer
- 56: spectral layer
- 58: light receiving layer
- 59: light receiving element
- 110: operation input unit
- 120: display unit
- 130: sound output unit
- 140: communication unit
- 210: irradiation unit
- 220: imaging unit
- 300: control unit
- 310: blood glucose level measurement unit
- 314: biological image acquisition unit
- 316: vascular pattern acquisition unit
- 318: vascular site selection unit
- 320: measurement-purpose light receiving and emitting unit selection unit
- 322: reference-purpose light receiving and emitting unit selection unit
- 324: absorption spectrum calculation unit
- 326: component value calculation unit
- 342: irradiation control unit
- 344: imaging control unit
- 400: storage unit
- 402: system program
- 404: blood glucose level measurement program
- 406: light emitting element list
- 408: light receiving element list
- 410: optimum distance data
- 414: biological image data
- 416: vascular pattern data
- 418: vascular site data
- 418*a*: vascular site ID
- 418*b*: site pixel list
- 418*c*: center line position information
- 418*d*: site length
- 418*e*: measurement-purpose light emitting unit data
- 418*f*: measurement-purpose light receiving unit data
- 418*g*: reference-purpose light emitting unit data
- 418*h*: reference-purpose light receiving unit data
- 420: absorption spectrum data
- 422: measured blood glucose level data
- J: distance
- L: light emitting unit
- L1, L2: straight line
- Ld: measurement-purpose light emitting unit
- Lr: reference-purpose light emitting unit
- O, Or, Os: light intensity
- P4: vascular pattern
- Q1: first light receiving result
- Q2: second light receiving result
- R2: light receiving region
- RL: light emitting region
- RL1: first light emitting region
- RL2: second light emitting region
- S: light receiving unit
- Sd: measurement-purpose light receiving unit
- Sr: reference-purpose light receiving unit
- T: transmittance
- W: interval

The invention claimed is:

1. A biological information acquisition device comprising:
a plurality of light emitting diodes that irradiate a living body with light;
light receiving sensors that receive the light transmitted through the living body; and
a processor that controls the light emitting diodes and the light receiving sensors, that acquires first biological information by causing the light receiving sensors to receive the light emitted by at least one light emitting diode in the plurality of light emitting diodes, and that acquires second biological information which is different from the first biological information by causing the light receiving sensors to receive the light emitted by the at least one light emitting diode in the plurality of light emitting diodes,
wherein a first light emitting power, when the first biological information is acquired, in a first light emitting region which is a first inner region defined by a first set of the light emitting diodes simultaneously emitting the light when the first biological information is acquired is weaker than a second light emitting power, when the second biological information is acquired, in a second light emitting region which is smaller than the first light emitting region and which is a second inner region defined by a second set of the light emitting diodes simultaneously emitting the light when the second biological information is acquired.

2. The biological information acquisition device according to claim 1,
wherein the second biological information includes vascular information of the living body.

3. The biological information acquisition device according to claim 1,
wherein the first biological information includes information for specifying a vascular position of the living body.

4. The biological information acquisition device according to claim 1, further comprising:
a battery that supplies energy to the light emitting diodes so as to emit the light.

5. The biological information acquisition device according to claim 1, further comprising:
a fixing band for wearing the biological information acquisition device on a wrist of the living body.

6. The biological information acquisition device according to claim 1,
wherein an OLED is used as each of the light emitting diodes.

7. The biological information acquisition device according to claim 1,
wherein the second biological information is glucose concentration in blood of the living body or oxygen saturation in the blood of the living body.

8. The biological information acquisition device according to claim 1,
wherein the first light emitting power is approximately $1/7$ of the second light emitting power.

9. A biological information acquisition device comprising:
a plurality of light emitting diodes that irradiate a living body with light;
light receiving sensors that receive the light transmitted through the living body; and
a processor that controls the light emitting diodes and the light receiving sensors, that acquires first biological information by causing the light receiving sensors to receive the light emitted by at least one light emitting diode in the plurality of light emitting diodes, and that acquires second biological information which is different from the first biological information by causing the light receiving sensors to receive the light emitted by the at least one light emitting diode in the plurality of light emitting diodes,
wherein a first power consumption, when the first biological information is acquired, in a first light emitting region which is a first inner region defined by a first set of the light emitting diodes simultaneously emitting the light when the first biological information is acquired is lower than a second power consumption, when the second biological information is acquired, in a second light emitting region which is smaller than the first light emitting region and which is a second inner region defined by a second set of the light emitting diodes simultaneously emitting the light when the second biological information is acquired.

10. The biological information acquisition device according to claim 9,
wherein a current flowing inside the first light emitting region when the first biological information is acquired is lower than a current flowing inside the second light emitting region when the second biological information is acquired.

11. The biological information acquisition device according to claim 9,
wherein the second biological information includes vascular information of the living body.

12. The biological information acquisition device according to claim 9,
wherein the first biological information includes information for specifying a vascular position of the living body.

13. The biological information acquisition device according to claim 9, further comprising:
a battery that supplies energy to the light emitting diodes so as to emit the light.

14. The biological information acquisition device according to claim 9, further comprising:
a fixing band for wearing the biological information acquisition device on a wrist of the living body.

15. The biological information acquisition device according to claim 9,
wherein an OLED is used as each of the light emitting diodes.

16. The biological information acquisition device according to claim 9,
wherein the second biological information is glucose concentration in blood of the living body or oxygen saturation in the blood of the living body.

17. A biological information acquisition method of acquiring biological information by using a biological information acquisition device including a plurality of light emitting diodes that irradiate a living body with light, and light receiving sensors that receive the light transmitted through the living body, the method comprising:
a step of acquiring first biological information by causing the light receiving sensors receive the light emitted by at least one light emitting diode in the plurality of light emitting diodes; and
a step of acquiring second biological information which is different from the first biological information by causing the light receiving sensors to receive the light emitted by the at least one light emitting diode in the plurality of light emitting diodes,
wherein a first light emitting power, when the first biological information is acquired, in a first light emitting region which is a first inner region defined by a first set of the light emitting diodes simultaneously emitting the light when the first biological information is acquired is weaker than a second light emitting power, when the second biological information is acquired, in a second light emitting region which is smaller than the first light emitting region and which is a second inner region defined by a second set of the light emitting diodes simultaneously emitting the light when the second biological information is acquired, or
wherein a first power consumption, when the first biological information is acquired, in the first light emitting region is lower than a second power consumption, when the second biological information is acquired, in the second light emitting region.

* * * * *